United States Patent

(12) United States Patent
Fan et al.

(10) Patent No.: US 12,733,833 B2
(45) Date of Patent: Sep. 15, 2026

(54) SYSTEMS AND METHODS FOR MR MULTITASKING-BASED DYNAMIC IMAGING FOR CEREBROVASCULAR EVALUATION

(71) Applicant: CEDARS-SINAI MEDICAL CENTER, Los Angeles, CA (US)

(72) Inventors: Zhaoyang Fan, Palos Verdes Estates, CA (US); Anthony Christodoulou, Los Angeles, CA (US); Debiao Li, South Pasadena, CA (US); Zhehao Hu, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 670 days.

(21) Appl. No.: 18/001,998

(22) PCT Filed: Jun. 16, 2021

(86) PCT No.: PCT/US2021/037695
§ 371 (c)(1),
(2) Date: Dec. 15, 2022

(87) PCT Pub. No.: WO2021/257742
PCT Pub. Date: Dec. 23, 2021

(65) Prior Publication Data

US 2023/0225628 A1 Jul. 20, 2023

Related U.S. Application Data

(60) Provisional application No. 63/039,882, filed on Jun. 16, 2020.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *A61B 5/0263* (2013.01); *G01R 33/50* (2013.01)

(58) Field of Classification Search
CPC ..... A61B 5/055; A61B 5/0042; A61B 5/0263; G01R 33/50; G01R 33/561; G01R 33/5601; G01R 33/56366
See application file for complete search history.

(56) References Cited

U.S. PATENT DOCUMENTS

| | | | | |
|---|---|---|---|---|
| 5,983,251 A | | 11/1999 | Martens | |
| 6,804,546 B1 * | | 10/2004 | Thompson ............ | A61B 5/055 324/309 |

(Continued)

OTHER PUBLICATIONS

Shaw, J. L., Yang, Q., Zhou, Z., Deng, Z., Nguyen, C., Li, D., & Christodoulou, A. G. (2019). Free-breathing, non-ECG, continuous myocardial T1 mapping with cardiovascular magnetic resonance multitasking. Magnetic resonance in medicine, 81(4), 2450-2463. (Year: 2019).*

(Continued)

*Primary Examiner* — Keith M Raymond
*Assistant Examiner* — Johnathan Maynard
(74) *Attorney, Agent, or Firm* — NIXON PEABODY LLP

(57) ABSTRACT

A method for performing magnetic resonance imaging on a subject comprises: injecting a contrast agent into a region of interest of the subject; applying a pulse sequence to the region of interest; collecting auxiliary data for the region of interest, the auxiliary data being related to one or more time-varying parameters of the subject within the region of interest; determining a temporal factor Φ from the auxiliary data; collecting imaging data for the region of interest, the imaging data being related to one or more spatially-varying parameters of the subject within the region of interest; determining a spatial factor Ur from the imaging data;
(Continued)

modeling a multi-dimensional image sequence as I=UrΦ; and deriving at least a first metric and a second metric from the multi-dimensional image sequence I, the first metric and the second metric being associated with distinct perfusion-based imaging techniques.

21 Claims, 16 Drawing Sheets

(51) Int. Cl.
*A61B 5/026* (2006.01)
*G01R 33/50* (2006.01)

(56) References Cited

U.S. PATENT DOCUMENTS

2010/0296714 A1* 11/2010 Schmainda .......... A61B 5/0263 382/131
2012/0177269 A1 7/2012 Lu
2012/0194193 A1* 8/2012 Rehwald ............ G01R 33/4828 324/318
2018/0306882 A1* 10/2018 Li ...................... G06V 10/7715
2019/0346523 A1 11/2019 Li

OTHER PUBLICATIONS

Wang, N., Christodoulou, A. G., Xie, Y., Wang, Z., Deng, Z., Zhou, B., . . . & Li, D. (2019). Quantitative 3D dynamic contrast-enhanced (DCE) MR imaging of carotid vessel wall by fast T1 mapping using Multitasking. Magnetic resonance in medicine, 81(4), 2302-2314. (Year: 2019).*

Wang, Y., Yu, Y., Li, D., Bae, K. T., Brown, J. J., Lin, W., & Haacke, E. M. (2000). Artery and vein separation using susceptibility-dependent phase in contrast-enhanced MRA. Journal of Magnetic Resonance Imaging, 12(5), 661-670. (Year: 2000).*

Ma, S., Nguyen, C. T., Han, F., Wang, N., Deng, Z., Binesh, N., . . . & Li, D. (2020). Three-dimensional simultaneous brain T1, T2, and ADC mapping with MR multitasking. Magnetic resonance in medicine, 84(1), 72-88. (Year: 2020).*

Christodoulou, A. G., Shaw, J. L., Nguyen, C., Yang, Q., Xie, Y., Wang, N., & Li, D. (2018). Magnetic resonance multitasking for motion-resolved quantitative cardiovascular imaging. Nature biomedical engineering, 2(4), 215-226. (Year: 2018).*

Wang, N., Gaddam, S., Wang, L., Xie, Y., Fan, Z., Yang, W., . . . & Li, D. (2020). Six-dimensional quantitative DCE MR multitasking of the entire abdomen: Method and application to pancreatic ductal adenocarcinoma. Magnetic resonance in medicine, 84(2), 928-948. (Year: 2020).*

Hu, Z., Christodoulou, A. G., Wang, N., Shaw, J. L., Song, S. S., Maya, M. M., . . . & Fan, Z. (2020). Magnetic resonance multitasking for multidimensional assessment of cardiovascular system: Development and feasibility study on the thoracic aorta. Magnetic resonance in medicine, 84(5), 2376-2388. (Year: 2020).*

Zampini, M. A., Buizza, G., Paganelli, C., Fontana, G., D'Ippolito, E., Valvo, F., . . . & Baroni, G. (2020). Perfusion and diffusion in meningioma tumors: a preliminary multiparametric analysis with dynamic susceptibility contrast and intravoxel incoherent motion MRI. Magnetic Resonance Imaging (Year: 2020).*

Zakariaee, S. S., Oghabian, M. A., Firouznia, K., Sharifi, G., Arbabi, F., & Samiei, F. (2018). Assessment of the agreement between cerebral hemodynamic indices quantified using dynamic susceptibility contrast and dynamic contrast-enhanced perfusion magnetic resonance imagings. J Clin Imaging Sci. (Year: 2018).*

Hutter, J., Slator, P. J., Christiaens, D., Teixeira, R. P. A., Roberts, T., Jackson, L., . . . & Hajnal, J. V. (2018). Integrated and efficient diffusion-relaxometry using ZEBRA. Scientific reports, 8(1), 15138. (Year: 2018).*

International Search Report and Written Opinion International Application No. PCT/US21/37695, mailed Sep. 28, 2021, pp. 13.

* cited by examiner

SYSTEMS AND METHODS FOR MR MULTITASKING-BASED DYNAMIC IMAGING FOR CEREBROVASCULAR EVALUATION

CROSS REFERENCE TO RELATED APPLICATIONS

This application is a U.S. National Stage of International Application No. PCT/US2021/037695, filed Jun. 16, 2021, which claims the benefit of, and priority to, U.S. Provisional Patent Application No. 63/039,882, filed Jun. 16, 2020, each of which is hereby incorporated by reference herein in its entirety.

TECHNICAL FIELD

The present disclosure relates biomedical imaging and analysis. More specifically, the present disclosure relates to magnetic resonance multitasking-based dynamic imaging using multiple imaging frameworks.

BACKGROUND

Magnetic resonance imaging has evolved into an increasingly common imaging modality for cerebrovascular evaluation. Several types of dynamic imaging can be used, including dynamic contrast enhanced (DCE) imaging, dynamic susceptibility contrast (DSC) imaging, and susceptibility weighted (SW) imaging. However, it can be impractical to separately perform each of these types of dynamic imaging during a single exam, due to the lengthy protocol required, and the potential for overdose of the injected contrast agent. Thus, there is a need for new systems and methods that can more efficiently and effectively perform multiple types of imaging in a single exam.

SUMMARY

According to aspects of the present disclosure, a method for performing magnetic resonance (MR) imaging on a subject comprises injecting a contrast agent into a region of interest of the subject; applying a pulse sequence to the region of interest of the subject; collecting auxiliary data for the region of interest of the subject, the auxiliary data being related to one or more time-varying parameters of the subject within the region of interest; determining a temporal factor $\Phi$ from the auxiliary data; collecting imaging data for the region of interest of the subject, the imaging data being related to one or more spatially-varying parameters of the subject within the region of interest; determining a spatial factor $U_r$ from the imaging data; modeling a multi-dimensional image sequence a $I=U_r\Phi$; and deriving at least a first metric and a second metric from the multi-dimensional image sequence I, the first metric and the second metric being associated with distinct perfusion-based imaging techniques.

According to aspects of the present disclosure, a system for performing magnetic resonance (MR) imaging on a subject comprises a magnet operable to provide a magnetic field; a transmitter operable to transmit to a region within the magnetic field; a receiver operable to receive a magnetic resonance signal from the region with the magnetic field; and one or more processors operable to control the transmitter and the receiver, the one or more processors being configured to cause the following method to be performed: injecting a contrast agent into a region of interest of the subject; applying a pulse sequence to the region of interest of the subject; collecting auxiliary data for the region of interest of the subject, the auxiliary data being related to one or more time-varying parameters of the subject within the region of interest; determining a temporal factor $\Phi$ from the auxiliary data; collecting imaging data for the region of interest of the subject, the imaging data being related to one or more spatially-varying parameters of the subject within the region of interest; determining a spatial factor $U_r$ from the imaging data; modeling a multi-dimensional image sequence a $I=U_r\Phi$; and deriving at least a first metric and a second metric from the multi-dimensional image sequence I, the first metric and the second metric being associated with distinct perfusion-based imaging techniques.

According to aspects of the present disclosure, a non-transitory machine-readable medium having stored thereon instructions for performing magnetic resonance (MR) imaging on a subject, which when executed by at least one processor, cause the following method to be performed: injecting a contrast agent into a region of interest of the subject; applying a pulse sequence to the region of interest of the subject; collecting auxiliary data for the region of interest of the subject, the auxiliary data being related to one or more time-varying parameters of the subject within the region of interest; determining a temporal factor $\Phi$ from the auxiliary data; collecting imaging data for the region of interest of the subject, the imaging data being related to one or more spatially-varying parameters of the subject within the region of interest; determining a spatial factor $U_r$ from the imaging data; modeling a multi-dimensional image sequence a $I=U_r\Phi$; and deriving at least a first metric and a second metric from the multi-dimensional image sequence I, the first metric and the second metric being associated with distinct perfusion-based imaging techniques.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1:
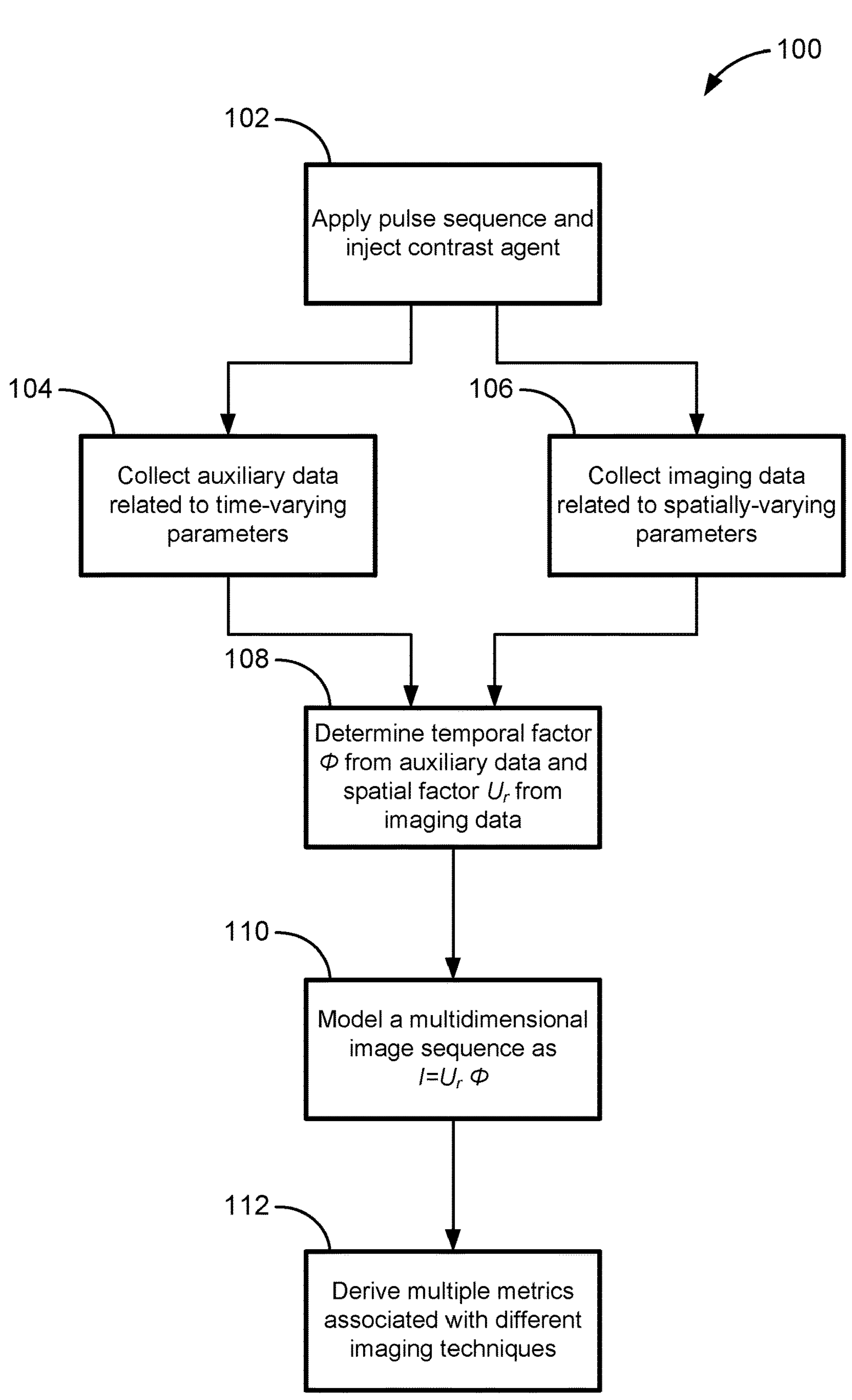
FIG. 1 shows a method for performing magnetic resonance imaging on a subject, according to aspects of the present disclosure.

While the present disclosure is susceptible to various modifications and alternative forms, specific implementations and embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

While the present disclosure has been described with reference to one or more particular embodiments or implementations, those skilled in the art will recognize that many changes may be made thereto without departing from the spirit and scope of the present disclosure. Each of these embodiments or implementations and obvious variations thereof is contemplated as falling within the spirit and scope of the present disclosure. It is also contemplated that additional embodiments or implementations according to aspects of the present disclosure may combine any number of features from any of the embodiments or implementations described herein.

Magnetic resonance-based imaging (MR imaging) is a technique most often used for imaging the human body that takes into account principles of nuclear magnetic resonance. For example, doctors and other medical professionals often use MR imaging to view tissue within the human body. Nuclear magnetic resonance is a phenomenon in which nuclei (such as protons in body tissue) localized in a magnetic field emit energy that can be detected. This energy that is detected can be used to create an image. MR imaging generally involves two principle steps. First, the magnetic moment of the nuclei (a vector property of a nucleus caused by the intrinsic spin property of elementary particles) are aligned (or polarized) by the presence of an external magnetic field. While in the presence of this external magnetic field, the magnetic moment of each nucleus will generally precess about an axis parallel to the magnetic field. The rate of this precession $\omega$ is generally proportional to $\gamma B_0$, where $B_0$ is the magnitude of the external magnetic field, and $\gamma$ is the gyromagnetic ratio of the nuclei, which is the ratio the nuclei's magnetic moment to its angular momentum. The rate of the precession $\omega$ is considered the nuclei's resonant frequency.

The second principle step in MR imaging is to apply an electromagnetic pulse sequence (usually a radiofrequency, or RF, pulse) to the nuclei. When the frequency of the RF pulses sequence is generally equal to the resonant frequency of the nuclei, the nuclei absorb the energy of the RF pulse and the magnetic moments are rotated out of alignment with the magnetic field. The magnetic moments of the excited nuclei eventually re-align within the presence of the external magnetic field in a process known as relaxation, which has two components, T1 and T2. T1 relaxation describes how the component of the magnetic moment parallel to the external magnetic field returns to its initial value. T2 relaxation describes how the components of the magnetic moment perpendicular to the external magnetic field return to their initial value. Because the magnetic moments of nuclei in the external magnetic field without the RF pulse sequence applied are generally parallel to the external magnetic field, T1 relaxation generally describes how parallel component of the magnetic moment returns to its maximum value, while T2 relaxation generally describes how the perpendicular components of the magnetic moment decay. The nuclei of different material relax at different rates and thus emit differing signals, which can be detected and used to form an image identifying the different materials.

Dynamic MR imaging can produce a spatiotemporal image sequence I(x, t), which is a function of (i) spatial location within the subject and (ii) one or more time-varying parameters related to the dynamic processes. The spatial location is denoted by vector $x=[x_1, x_2, x_3]^T$, which contains up to three spatially-varying parameters $x_i$. The time-varying parameters are denoted by vector $t=[t_1, t_2, \ldots, t_R]^T$ containing R time-varying independent variables $t_i$. The imaging data obtained from the MR imaging is generally from a specific region of interest of the subject. In an example, the region of interest could be the subject's abdomen or chest. In other examples, the region of interest of the subject is more specific. For example, the region of interest could be an organ, such as the subject's liver, lungs, heart, pancreas, brain, prostate, breast, or any other organ.

The imaging data is dependent on or related to the spatially-varying and time-varying parameters of the region of interest of the subject referred to above. The spatially-varying parameters include a voxel location, a contrast agent kinetic parameter, or a diffusion parameter (which includes changing strength, changing direction, or both). The spatially-varying parameters can additionally or alternatively be related to physical motion of the region of interest of the subject. The time-varying parameters can include, but is not limited to: the phase of the subject's heart within a cardiac cycle; the position of the subject's lungs, chest wall, or other organs within a respiratory cycle; a position of a dome of a liver during respiration; relaxation time parameters such as T1, T1ρ (also known as T1-rho), T2, T2* (also known as T2-star, which is similar to T2 but is modified based on inhomogeneities in the magnetic field used during the imaging sequence), relaxation rate parameters, an inversion time (or other time since magnetization preparation); a diffusion weighting strength; a diffusion weighting direction; an echo time; a dynamic contrast enhancement phase; a flip angle; an elapsed time since the start of scanning; elastographic wave propagation, a phase offset of elastographic excitation waves; a frequency offset and duration of saturation preparation pulses (e.g., for chemical exchange saturation transfer); a duration of magnetization transfer preparation pulses; a chemical exchange saturation transfer, a spectral position (e.g., for spectroscopy); a flow encoding strength; a flow encoding direction; free induction decay, or the general passage of time. The relaxation time parameters (including T1 and T2*) describe a relaxation time. The relaxation rate parameters describe a relaxation rate, and are generally the inverse of their relaxation time counterparts. Thus, T1 describes the T1 relaxation time, and R1=1/T1 describes the T1 relaxation rate. Similarly, T2* describes the T2* relaxation time, and R2*=1/T2* describes the T2* relaxation rate.

Some of the spatially-varying parameters can also be time-varying, and some of the time-varying parameters can also be spatially-varying. For example, cardiac motion is generally a time-varying parameter, while the relaxation parameters, the contrast agent kinetic parameter, and the diffusion parameter are generally time-varying. Generally, the imaging data is indicative of the value or magnitude of the spatially-varying parameters and/or the time-varying parameters. In another example, the region of interest is the subject's abdomen containing their liver, and the spatially-varying parameter that is being measured is the $T_1$ relaxation parameter. The $T_1$ relaxation parameter can be spatially-varying, meaning that the value of the $T_1$ relaxation parameter at a first physical location within the subject's liver can be different than the value of the $T_1$ relaxation parameter at a second physical location within the subject's liver. In a resulting image showing the value measured $T_1$ relaxation parameter, different locations in the image (corresponding to different physical locations within the subject's liver) will show different values. In some implementations, the spatially-varying parameters can also be time-varying. In other implementations, the spatially-varying parameters can additionally or alternatively be related to physical motion of the region of interest of the subject. In general, the techniques disclosed herein can be used to perform dynamic imaging that resolves parameters that can vary across space and time.

The image sequence can be represented as a matrix $I=U_r\psi$. In this formulation, $U_r \in C^{J \times L}$ contains L spatial weighting functions with J total voxels and is known as a spatial factor, whereas $\Phi \in C^{L \times N_t}$ contains temporal basis functions, and is known as the temporal factor. $U_r$ contains one or more spatial weighting functions that describe the properties of the spatially-varying parameters. $U_r$ is formed as a spatial factor matrix. $\Phi$ contains one or more temporal basis functions that describe the properties of the time-varying parameters. $\Phi$ is formed as a temporal factor matrix when imaging with only a single time dimension is used, and is formed as a temporal factor tensor when imaging with multiple time dimensions is used. At any point in time t, the image can be expressed as a linear combination of the spatial factor $U_r$, weighted by the temporal factor $\Phi_t$, which is the column of $\Phi$ corresponding to time point t.

Perfusion MR imaging is a type of MR imaging that tracks the passage of a fluid through an organ, tissue, etc. Cerebrovascular perfusion imaging is a common modality for evaluating a variety of cerebrovascular diseases, such a strokes and brain tumors. Different types of cerebrovascular-oriented perfusion imaging techniques exist, including dynamic contrast enhanced (DCE) imaging, and dynamic susceptibility contrast (DSC) imaging. DCE imaging is useful for quantifying any disruptions of the blood-brain barrier. DSC imaging is useful for assessing perfusion defects. Other types of non-perfusion cerebrovascular imaging are also commonly used, such as susceptibility weighted (SW) imaging. SW imaging is useful for detecting intracerebral hemorrhages or micro-bleeding. Performing each of these types of cerebrovascular imaging scans is ideal for monitoring a subject's cerebrovascular condition. However, performing separate scans is generally impractical, due to the long length of time required, and the potential for overdose of the contrast agent.

Referring now to FIG. 1, a flowchart illustrating the steps of a method 100 for performing MR imaging is shown. At step 102, a contrast agent is injected into the region of interest of the subject, and a pulse sequence is then applied. In some implementations, the contrast agent is injected after the application of the pulse sequence begins. For example, the contrast agent can be injected about one minute after application of the pulse sequence begins. In other implementations, the contrast agent is injected before application of the pulse sequence begins, or as the application of the pulse sequence begins. Any suitable MR contrast agent can be used, such as gadobutral (i.e., Gadovist or Gadavist), gadopentetate (i.e., gadopentetic acid or Magnevist), or others. The pulse sequence is designed to recover data that can be used for multiple different imaging modalities, such as DCE imaging, DSC imaging, and SW imaging.

Figure 2:
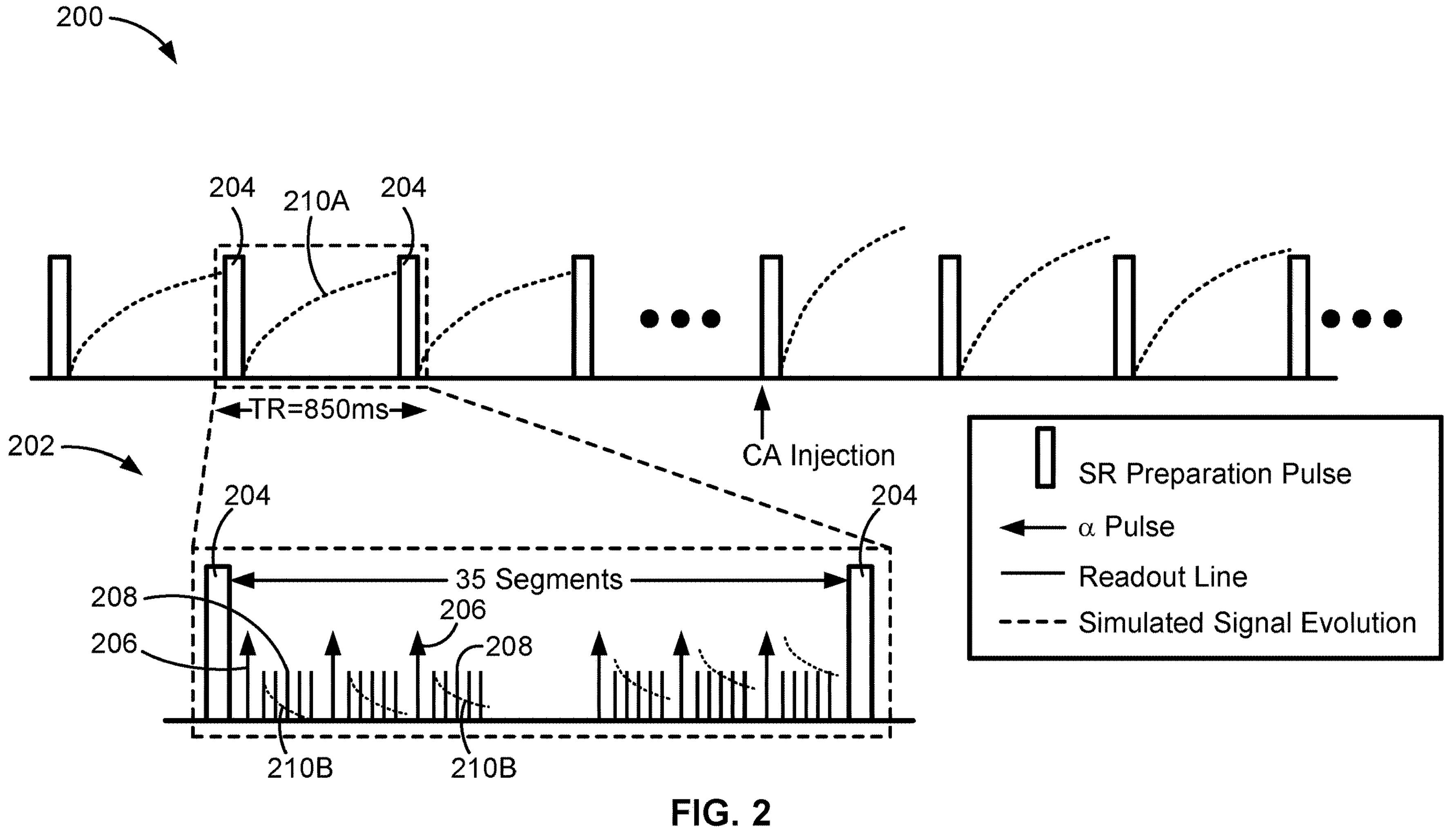
FIG. 2 shows an example pulse sequence for use with the method of FIG. 1, according to aspects of the present disclosure.

FIG. 2 shows an example pulse sequence 200 that can be used at step 102 of method 100. The pulse sequence 200 includes one or more repetition time periods TR, with a specific pulse sub-sequence 202 being repeated every repetition time period TR. In some implementations, the pulse sub-sequence 202 that is applied each repetition time period TR includes a non-selective saturation recovery preparation pulse 204 to generate T1 recovery along the magnetization z-axis, one or more excitation pulses 206 (also referred to as an alpha pulse), and one or more readout lines 208 (also referred to as readouts, readout pulses, echo pulses, echo readouts, or echo readout pulses). FIG. 2 includes a zoomed-in view of the pulse sub-sequence 202 of one repetition time period TR that includes the preparation pulse 204, the excitation pulses 206, and the readout lines 208, as well as the preparation pulse 204 for the next repetition time period TR.

In the illustrated implementation, the one or more excitation pulses 206 of the pulse sub-sequence 202 and the one or more readout lines 208 of the pulse sub-sequence 202 include a plurality of excitation pulses 206, and a set of readout lines 208 following each single excitation pulse. Each single excitation pulse 206 and the readout lines 208 following that single excitation pulse 206 can form a multi-echo FLASH readout. In some implementations, every single one of the excitation pulses 206 is followed by five readout lines 208. In some implementations, the pulse sub-sequence 202 includes at least one excitation pulse 206, and at least one set of readout lines 208, with each set of readout lines 208 following one of the excitation pulses 206. Each set of readout lines 208 can include two or more readout lines 208. In some implementations, every pulse sub-sequence 202 that is applied during each repetition time period TR includes one preparation pulse 204, thirty-five excitation pulses 206, and 175 readout lines 208 (five readout lines 208 following each of the thirty-five excitation pulses 206). As is shown, one or more pulses sub-sequences 202 can be applied before and after the injection of the contrast agent. FIG. 2 also shows the simulated signal evolution during the application of the pulse sequence 200. Following each preparation pulse 204, the simulated signal 210A follows an upward-sloping trajectory, depicting the T1 recovery process. Following each excitation pulse 206, the simulated signal 210B follows a downward-sloping trajectory, depicting T2* decay. The starting point of each simulated signal 210B within each pulse sub-sequence 202 is based on the current state of the simulated signal 210A during the same pulse sub-sequence 202.

Other types of pulse sequences can also be used. However, any pulse sequence used generally includes two features. First, the pulse sequence is configured to generate both T1-weighted and T2*-weighted contrasts, which—as discussed herein—allows for multiple types of imaging to be performed simultaneously from a pulse sequence. Second, the pulse sequence is configured generate multiple T1 weightings and multiple T2* weightings, with each contrast mechanism conceptualized as separate time dimensions. The multiple T1 weighting and T2* weightings allow for direct quantification of T1 and T2* relaxation times. The pulse sequence can have a variety of different properties, so long as these two features are present. For example, in some implementations, the pulse sequence includes fast low-angle shot (FLASH) readouts, which are free from the distortion effect caused by B0 inhomogeneities that can affect some types of readouts.

Referring back to FIG. 1, at step 104 of method 100, auxiliary data is collected in response to the pulse sequence being applied. The auxiliary data is related to one or more time-varying parameters of the region of interest of the subject, and is generally indicative of the value or magnitude of the time-varying parameters. At step 106 of method 100, imaging data is collected in response to the pulse sequence being applied. The imaging data is related to one or more spatially-varying parameters of the region of interest of the subject, and is generally indicative of the value or magnitude of the spatially-varying parameters. In one implementation, the parameters include T1 recovery, T2* decay, and the contrast enhancement time course, which are generally considered to be time-varying parameters. In some implementations, the auxiliary data and the imaging data are collected in real-time as the pulse sequence is being applied. The auxiliary data and the imaging data can be collected simultaneously during application of the pulse sequence, or can be collected at distinct times during application of the pulse sequence. Steps 104 and 106 can be performed in a variety of different manners. In some implementations, steps 104 and 106 are performed simultaneously, such that the auxiliary data and the imaging data is collected simultaneously. In other implementations, steps 104 and 106 are performed in an interleaved fashion, such that portions of the auxiliary data and portions of the imaging data are alternatively collected. In still other implementations, steps 104 and 106 are performed sequentially in either order, such that either (i) all of the auxiliary data is collected and then all of the imaging data is collected, or (ii) all of the imaging data is collected and then all of the auxiliary data is collected.

At step 108, a temporal factor $\Phi$ is determined from the auxiliary data, and the spatial factor $U_r$ is determined from the imaging data. In some implementations, the spatial factor $U_r$ is determined by fitting the temporal factor $\Phi$ to the imaging data, according to the following equation:

$$\hat{U}_r = \operatorname{argmin}_{U_r} \|d - \Omega[EU_r\Phi]\|_2^2 + \lambda R(U_r). \tag{1}$$

In this equation, d is the acquired imaging data, $\Omega$ is an undersampling pattern, E is a signal model, R(•) is the regularization function, and $\lambda$ is the regularization parameter for the regularization function R(•). In some implementations, R(•) is a spatial wavelet sparsity penalty or a spatial total variation constraint. Once the spatial factor $U_r$ is determined, the multidimensional image sequence is modeled at step 110. Generally, every image of the image sequence is a function of position and any time-varying parameters. In an implementation where T1 recovery, T2* decay, and the contrast enhancement time course are being analyzed, the multidimensional image sequence is denoted as $I(r, t_{T1}, t_{T2}^*, t_{CE})$, where $t_{T1}$ refers to T1 recovery, $t_{T2}^*$ refers to T2* decay, and $t_{CE}$ refers to the contrast enhancement time course. The image sequence $I(r, t_{T1}, t_{T2}^*, t_{Ce})$ can be modeled as a low-rank tensor, which can be factorized and expressed in matrix form as $I=U_r\Phi$, as noted above.

Finally, at step 112, multiple metrics, images, maps, etc. corresponding to different imaging techniques can be derived using the data acquired from the single pulse sequence. In some implementations, the metrics correspond to different imaging techniques, which could include perfusion-based imaging techniques, non-perfusion-based imaging techniques, or any combination of perfusion-based imaging techniques and non-perfusion-based imaging techniques. In some implementations, these imaging techniques are DCE imaging, DSC imaging, and SW imaging. In some implementations, the metrics quantify the concentration of the contrast agent based on dynamic T1 and T2* mapping, which is generally more accurate than linearly approximating the concentration of the contrast agent based on the signal intensity (which can have inaccuracies if the linear approximation between contrast concentration curves and the change in signal intensity is not well established).

In some implementations, step 112 includes generating dynamic T1 and T2* maps from the auxiliary data and the imaging data (e.g., from $U_r\Phi$), by exploiting the correlation between brain images along the different time dimensions.

The auxiliary data and the imaging data can be fit to a signal equation, which describes a value S at each voxel of the image (e.g., at each voxel of $I=U_r\Phi$). Essentially, the values of $I=U_r\Phi$ at each voxel are associated with the value of the signal equation at each voxel. The signal equation is given below:

$$S(A, \alpha, B, n, TE, T1(t), T2^*(t)) = A\frac{1-e^{-\frac{TR}{T1(t)}}}{1-e^{-\frac{TR}{T1(t)}}\cos(\alpha)}\left[1+(B-1)\left(e^{-\frac{TR}{T1(t)}}\cos(\alpha)^n\right]e^{-\frac{TE}{T2^*(t)}}\sin(\alpha). \quad (2)$$

Here, S is the value of the signal equation at each voxel (e.g., the intensity of the RF signal received from the tissue at the voxel), A is an amplitude term associated with the density of absorbing protons in the tissue and the sensitivity of the RF receiving antennas, a is the flip angle of the excitation pulses (such as excitation pulses 206), n is the number of excitation pulses in the pulse sequence that is applied to the tissue (such as the pulse sequence 200) since the previous preparation pulse (such as preparation pulses 204), and TE is the time between the center of the most recent excitation pulse and the center of the readout line (such as readout lines 208) in the pulse sequence applied to the tissue (such as the pulse sequence 200) which is also referred to as the echo time. Thus, dynamic T1 and T2* maps can be generated by fitting the above equation, when a given voxel of $I=U_r\Phi$ is substituted for S.

Figure 3A:
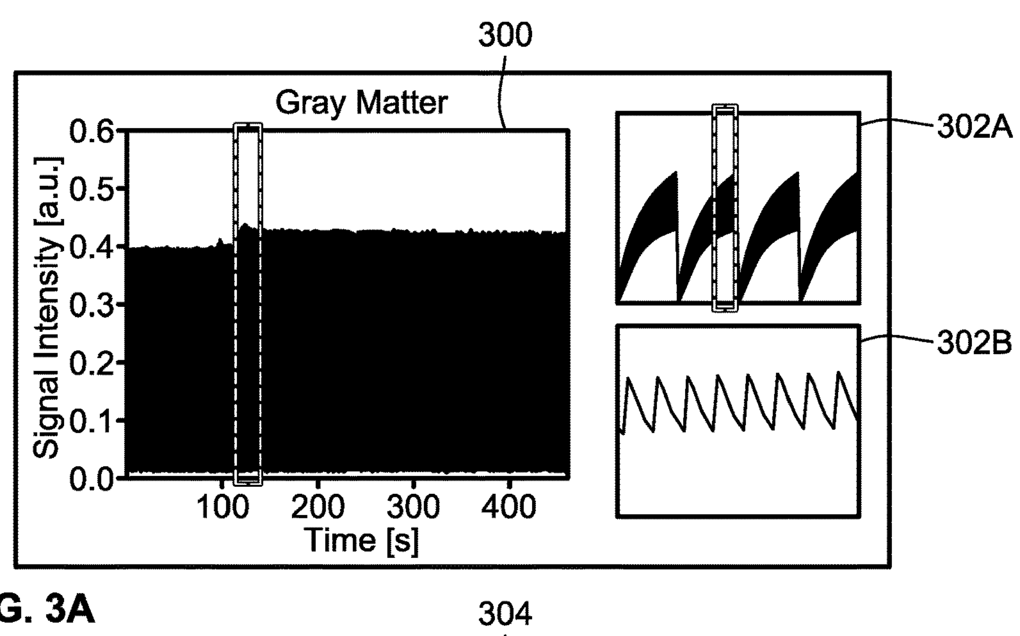
FIG. 3A shows a signal intensity plot for gray matter in a subject's brain, according to aspects of the present disclosure.
Figure 3B:
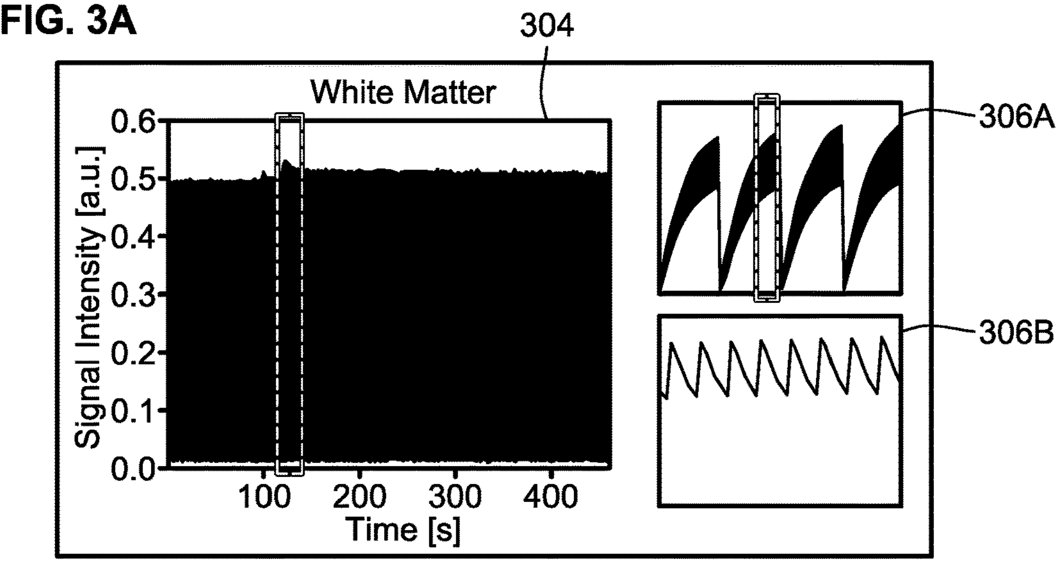
FIG. 3B shows a signal intensity plot for white matter in a subject's brain, according to aspects of the present disclosure.
Figure 3C:
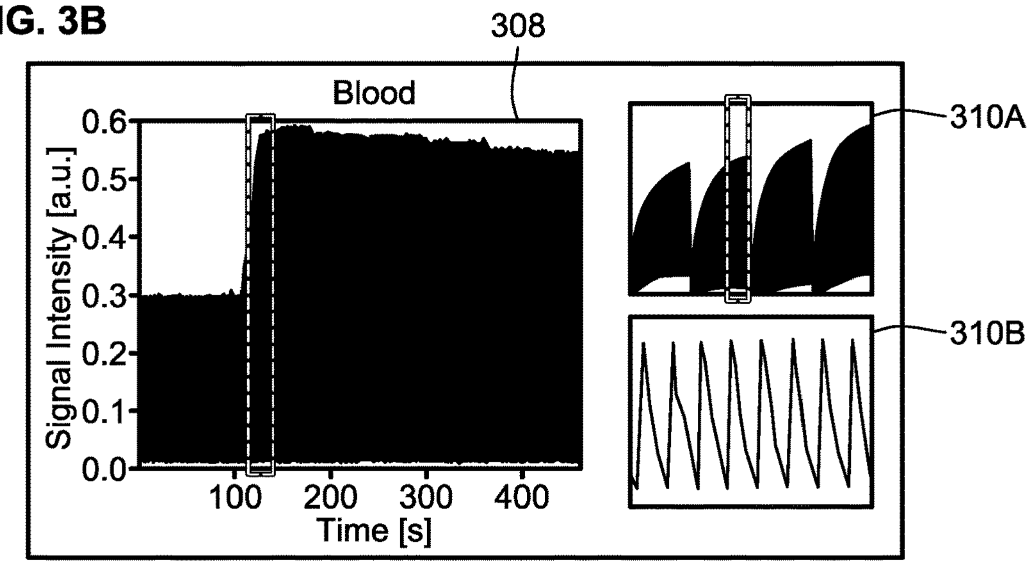
FIG. 3C shows a signal intensity plot for blood in a subject's brain, according to aspects of the present disclosure.

FIGS. 3A, 3B, and 3C show plots of the signal intensity (e.g., the value of S) generated by imaging a subject's brain. FIG. 3A shows a plot 300 of the signal intensity in the gray matter of the subject's brain. Inset plot 302A shows a zoomed-in view of the identified portion of plot 300, and inset plot 302B shows a zoomed-in view of the identified portion of inset plot 302A. Inset plot 302A shows the saturation recovery curves, and inset plot 302B shows the multi-echo FLASH readouts during contrast agent injection.

FIG. 3B shows a plot 304 of the signal intensity in the white matter of the subject's brain. Inset blot 306A shows a zoomed-in view of the identified portion of plot 304, and inset plot 306B shows a zoomed-in view of the identified portion of inset plot 306A. Inset plot 306A shows the saturation recovery curves, and inset plot 306B shows the multi-echo FLASH readouts during contrast agent injection.

FIG. 3C shows a plot 308 of the signal intensity in the blood of the subject's brain. Inset plot 310A shows a zoomed-in view of the identified portion of plot 308, and inset plot 310B shows a zoomed-in view of the identified portion of inset plot 310A. Inset plot 310A shows the saturation recovery curves, and inset plot 310B shows the multi-echo FLASH readouts during contrast agent injection.

Figure 3D:
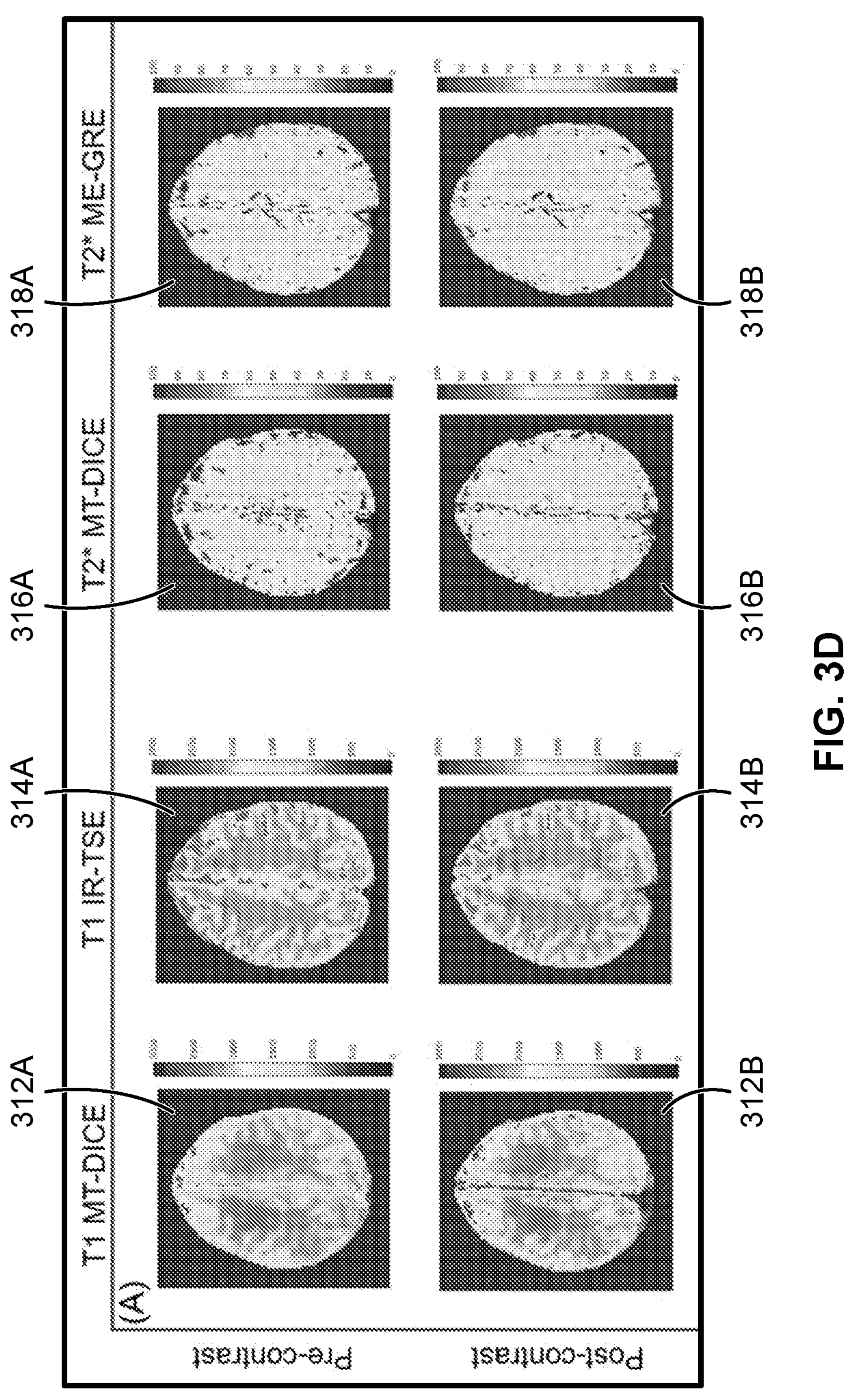
FIG. 3D shows dynamic T1 and T2* maps acquired from the signal intensity plots of FIGS. 3A, 3B, and 3C1, according to aspects of the present disclosure.

FIG. 3D shows example dynamic T1 maps and T2* maps. T1 maps 312A and 312B were acquired using method 100, while T1 maps 314A and 314B were acquired using a conventional reference method, such as inversion-recovery turbo spin echo (IR TSE). T2* maps 316A and 316B were acquired using method 100, while T3* maps 318A and 318B were acquired using a conventional reference method, such as multi-echo gradient recalled echo (ME GRE). The top map of each set of maps (e.g., maps 312A, 314A, 316A, and 318A) is representative of pre-contrast imaging, while the bottom map of each set of maps (e.g., maps 312B, 314B, 316B, and 318B) is representative of post-contrast imaging. These T1 and T2* maps show the T1 and T2* values at every location in an image. In FIG. 3D, the T1 and T2* maps show the T1 and T2* values in the subject's brain. As can be seen in FIG. 3D, the T1 and T2* maps generated using method 100 are comparable to T1 and T2* maps generated using conventional methods.

Figures 3E, 3F:
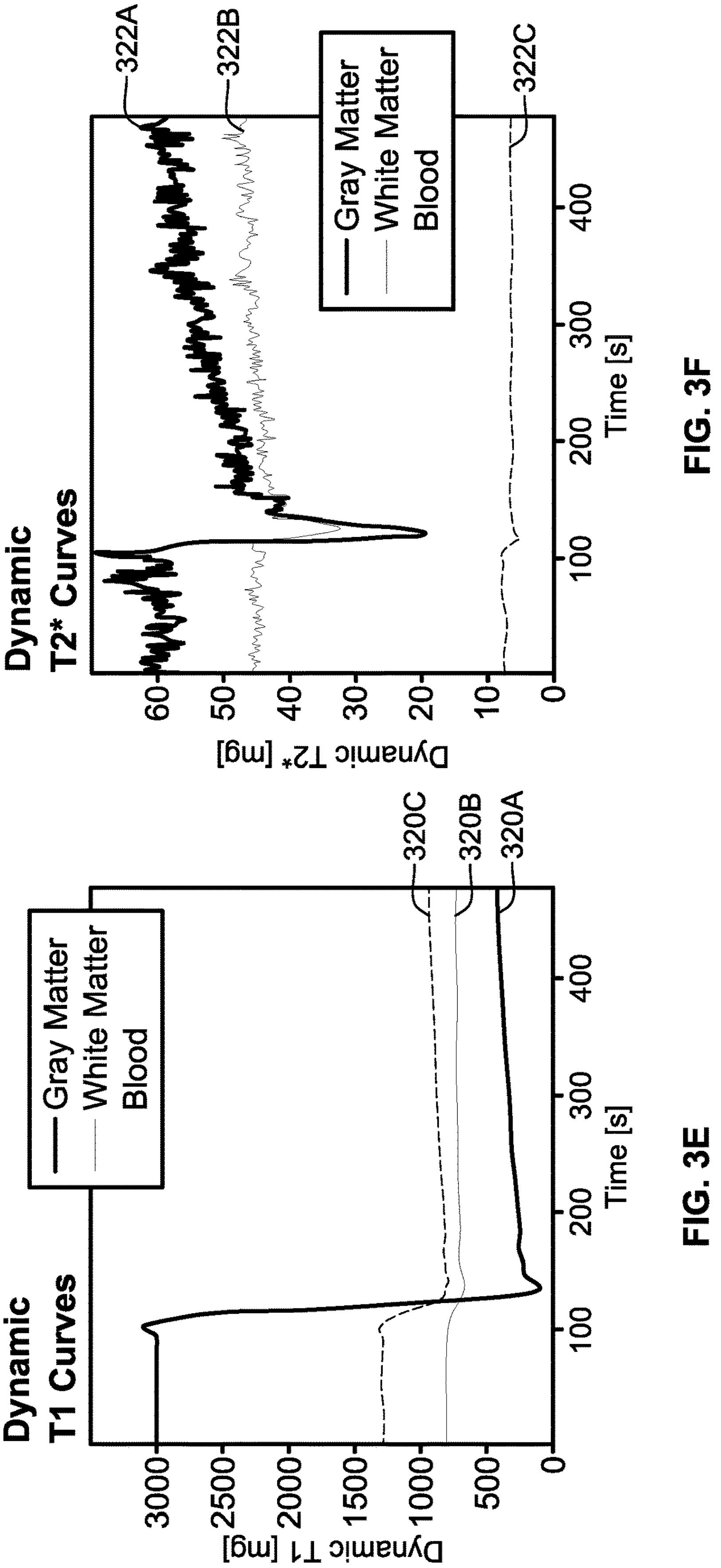
FIG. 3E shows a set of dynamic T1 curves acquired using the dynamic T1 maps of FIG. 3D, according to aspects of the present disclosure.
FIG. 3F shows a set of dynamic T2* curves acquired using the dynamic T2* maps of FIG. 3D, according to aspects of the present disclosure.

Once the dynamic T1 and T2* maps are determined, a dynamic T1 curve T1(t) and a dynamic T2* curve T2*(t) can be determined from the T1 and T2* maps. The dynamic T1 and T2* curves show the T1 and T2* values versus time at different locations of the subject. FIG. 3E shows an example set of dynamic T1 curves 320A, 320B, and 320C, while FIG. 3F shows an example set of dynamic T2* curves 322A, 322B, and 322C. These curves can be generated from T1 and T2* maps, respectively, such as the T1 and T2* maps in FIG. 3D. Thus, the dynamic T1 curves 320A-320C and the dynamic T2* curves 322A-322C show the T1 and T2* values versus time in the subject's brain. T1 curve 320A shows T1 values in the gray matter of the subject's brain. T1 curve 320B shows T1 values in the white matter of the subject's brain. T1 curve 320C shows T1 values in the blood of the subject's brain. Similarly, T2* curve 322A shows T2* values in the gray matter of the subject's brain, T2* curve 322B shows T2* values in the white matter of the subject's brain, and T2* curve 322C shows T2* values in the blood matter of the subject's brain.

Referring back to step 112, in some implementations, the metric associated with DCE imaging can be one or more of a fractional plasma volume $v_p$ of the region of interest, a fractional extravascular-extracellular volume $v_e$ of the region of interest, or a transfer constant $K^{trans}$ of the region of interest. These metrics can be referred to as kinetic parameters, and can be obtained using the dynamic T1 and T2* curves, such as T1 curves 320A-320C and T2* curves 322A-322C. To derive these metrics, a T1-based contrast concentration curve is determined according to:

$$C^{R1}(t) = \frac{1}{r_1}\left(\frac{1}{T1(t)} - \frac{1}{T1_{pre}}\right). \quad (3)$$

Figures 3G, 3H:
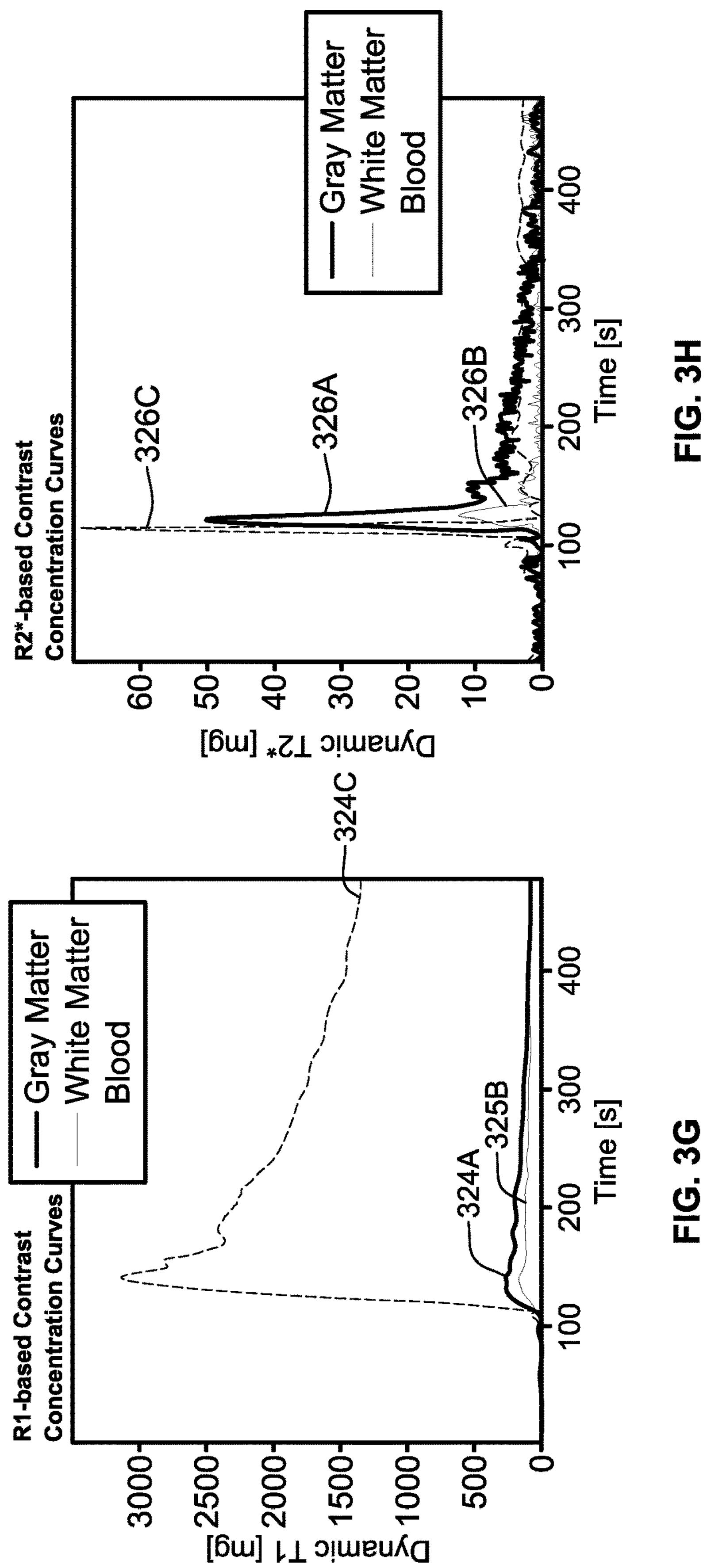
FIG. 3G shows a set of R1-based contrast concentration curves acquired using the dynamic T1 curves of FIG. 3E, according to aspects of the present disclosure.
FIG. 3H shows a set of R2*-based contrast concentration curves acquired using the dynamic T2* curves of FIG. 3F, according to aspects of the present disclosure.

Here, $C^{R1}(t)$ is the T1-based contrast concentration curve, which is a measure of the concentration of the injected contrast agent as a function of time. T1(t) is the dynamic T1 curve, $T1_{pre}$ is the T1 value before the contrast agent is injected, and $r_1$ is the longitudinal relaxivity of the contrast agent. FIG. 3G shows R1-based contrast concentration curves 324A (gray matter), 324B (white matter), and 324C (blood), which can be derived from the dynamic T1 curves 320A-320C in FIG. 3E using the above equation for $C^{R1}(t)$. As noted herein, R1 describes T1 relaxation rate, and is equal to the inverse of relaxation time T1. Thus, concentration curves 324A-324C describe the concentration of the contrast agent based on the T1 parameter. The kinetic parameters ($v_p$, $v_e$, and $K^{trans}$) can then be derived according to:

$$C_t^{R1}(t) = v_p C_p^{R1}(t) + K^{trans}\int_0^t C_p^{R1}(\tau)e^{-\left(\frac{K^{trans}}{v_e}\right)}d\tau. \quad (4)$$

Here, $$C_t^{R1}(t)$$

is the T1-based concentration of the contrast agent in tissue, and $$C_p^{R1}(t)$$

is the T1-based concentration of the contrast agent in plasma. The tissue being images generally consists of three components: parenchymal cells, blood vessels and arteries, and extracellular extravascular space (EES). The contrast agent diffuses between the blood vessels/arteries and the EES.

$$C_t^{R1}(t)$$

is determined by solving for $C^{R_1}(t)$ in equation (3) above in a region of the tissue containing the parenchymal cells.

$$C_p^{R1}(t)$$

is determined by solving for $C^{R_1}(t)$ in equation (3) above in a region of the tissue containing a select feeding artery. The kinetic parameters ($v_p$, $v_e$, and $K^{trans}$) can then be fitted from $$C_t^{R1}(t) \text{ and } C_p^{R1}(t).$$

In some implementations, the metric associated with DSC imaging is a leakage-corrected cerebral blood volume (CBV) measurement or a leakage-corrected cerebral blood flow (CBF) measurement. To derive the CBV and CBF measurements, the T2*-based contrast concentration curve $$C^{R_2^*}(t)$$

is first derived according to:

$$C^{R_2^*}(t) = \frac{1}{r_{2,p}^*}\left(\left(\frac{1}{T2^*(t)} - \frac{1}{T2^*_{pre}}\right) - r_{2,e}^* \cdot K^{trans} \cdot \exp\left(-\frac{K^{trans}}{v_e}t\right)\right). \quad (5)$$

Here, T2*(t) is the dynamic T2* curve, $$T2^*_{pre}$$

is the T2* value before the contrast agent is injected $$r_{2,p}^*$$

is the transverse relaxivity within the intravascular-extracellular space, and $$r_{2,e}^*$$

is the transverse relaxivity within the extravascular-extracellular space. FIG. 3H shows R2*-based contrast concentration curves 326A (gray matter), 326B (white matter), and 326C (blood), which can be derived from the dynamic T2* curves 322A-322C in FIG. 3F using the above equation for $$C^{R_2^*}(t).$$

As noted herein, R2* describes T2* relaxation rate, and is equal to the inverse of relaxation time T2*. Thus, concentration curves 326A-326C describe the concentration of the contrast agent based on the T2* parameter. The R2*-based contrast concentration curve $$C^{R_2^*}(t)$$

can than be used to determine both the T2*-based concentration of the contrast agent in a feeding artery $$C_a^{R2^*(t)}$$

and the T2*-based concentration of the contrast agent in the tissue $$C_t^{R2^*(t)}.$$

The CBV and CBF measurements can then be derived according to the following equations:

$$CBV = \frac{100}{\rho} \cdot \frac{(1-H_{SV})}{(1-H_{LV})} \cdot \frac{\int C_t^{R2^*(t)}(t)dt}{\int C_a^{R2^*(t)}(t)dt}, \text{ and} \quad (6)$$

$$CBF = 60 \cdot \frac{100}{\rho} \cdot \frac{(1-H_{SV})}{(1-H_{LV})} \cdot \left[\max\left(C_t^{R2^*}(t) \otimes^{-1} C_a^{R2^*}(t)\right)\right]. \quad (7)$$

Here, ρ is the density of the brain of the subject being imaged, $H_{SV}$ is a correction to the volume hematocrit level in small blood vessels such as capillaries due to the Fahreus-Lindquist effect, $H_{LV}$ is a correction to the volume hematocrit level in large blood vessels due to the Fahreus-Lindquist effect, and $\otimes^{-1}$ is a deconvolution operation. In some implementations, values of ρ=1.04 g/mL, $H_{SV}$=0.25, and $H_{LV}$=0.45 can be used.

The metric associated with SW imaging can be one or more SW images. Generally, magnitude and phase information are independently processed and combined to generate the one or more SW images. In some implementations, each of the one or more SW images are generated by taking an image from one of the readout lines 208 of pulse sequence 200, and multiplying the magnitude of that image by a corresponding phase mask, which is created and scaled from the filtered phased images over a 0-1 range. In some implementations, the images that the phase mask is applied to are generated from the final readout line 208 of each set of readout lines 208 within each of the pulse sub-sequences 202 that form pulse sequence 200. In other implementations, the images that the phase mask is applied to are generated from at least one readout line 208 of at least one set of readout lines 208 within at least one of the pulse sub-sequences 202 forming pulse sequence 200.

Thus, method 100 can be used to determine the value of multiple different metrics that would otherwise require multiple imaging sequences, longer scan times, and/or multiple injections of contrast agent. Conventional techniques for determining multiple different metrics often require multiple imaging sequences, multiple contrast injections, and a long scan time, which can lead to inter-scan motion that prevents metrics from being accurately determined, and prevents accurate analysis of the tissue being imaged. Moreover, multiple doses of contrast agent can pose health risks, such as allergic reaction, nephrogenic systemic fibrosis, and/or contrast deposition in the tissue being imaged (such as the user's brain). Method 100 can thus avoid the problems presented by conventional imaging protocols, and allows for many different metrics to be derived using a single image sequence and a single injection of a contrast agent.

In some implementations of method 100, any of the dynamic T1 and T2* maps in FIG. 3D, the dynamic T1 and T2* curves in FIGS. 3E and 3F, and the R1- and R2*-based contrast concentration curves in FIGS. 3G and 3H can be visually reproduced. In other implementations, the actual maps and curves are not visually reproduced, and only the data for the maps and curves is generated and used. In some implementations, the dynamic T1 and T2* curves are not generated from the dynamic T1 and T2* maps, but instead are generated directly from the signal equation described herein.

Moreover, in some implementations, the various maps and curves and/or the data used to generate the various maps and curves, can be inverted to describe relaxation rates instead of relaxation times, or to describe relaxation times instead of relaxation rates. For example, the T1 and T2* maps in FIG. 3D could alternatively be generated as R1 and R2* maps. In another example, the dynamic T1 and T2* curves in FIGS. 3E and 3F could alternatively be generated as dynamic R1 and R2* curves. In a further example, the R1- and R2*-based contrast concentration curves in FIGS. 3G and 3H could alternatively be generated as T1- and T2*-based contrast concentration curves.

In one example experiment utilizing method 100, subjects were scanned on a 3.0 T system with a 20-channel head-neck coil. In this example experiment, the following parameters were used: field of view=265×220 $mm^2$; in-plane spatial resolution=1.5×1.5 $mm^2$; 30 slices with 4-millimeter thickness; repetition time period=850 milliseconds; echo time period=2.46/7.38/12.30/17.22/22.14 milliseconds; flip angle=10°; total time=8 minutes; and Gadavist (0.1 mmol/kg) as the contrast agent injected three minutes into the scan at a rate of 3.0 milliliters/seconds.

Figure 4A:
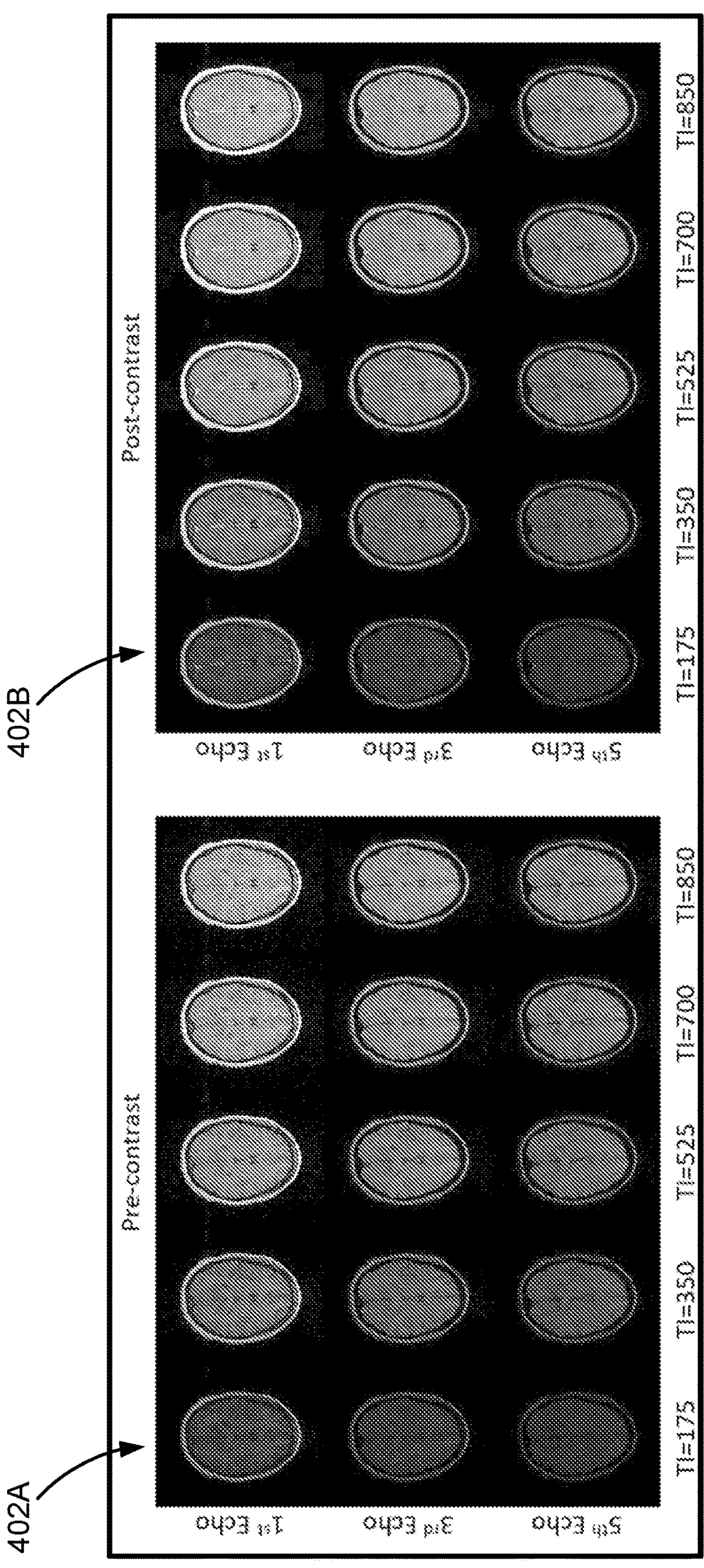
FIG. 4A shows a first example of images constructed using the method of FIG. 1, according to aspects of the present disclosure.

FIG. 4A shows example images obtained using method 100. FIG. 4 compares pre-contrast images 402A on the left (obtained using method 100 but without injection of the contrast agent) and post-contrast images 402B on the right (obtained using method 100), for different saturation recovery times. For both the pre-contrast images and post contrast images, the top row of images corresponds to the image following the first readout, the middle row corresponds to the image following the third readout, and the bottom row corresponds to the image following the fifth readout. For both the pre-contrast images and the post-contrast images, the first column from the left corresponds to TI=175 milliseconds (ms), the second column from the left corresponds to TI=350 ms, the third column from the left corresponds to TI=525 ms, the fourth column from the left corresponds to TI=700 ms, and the fifth column from the left corresponds to TI=850 ms.

Figure 4B:
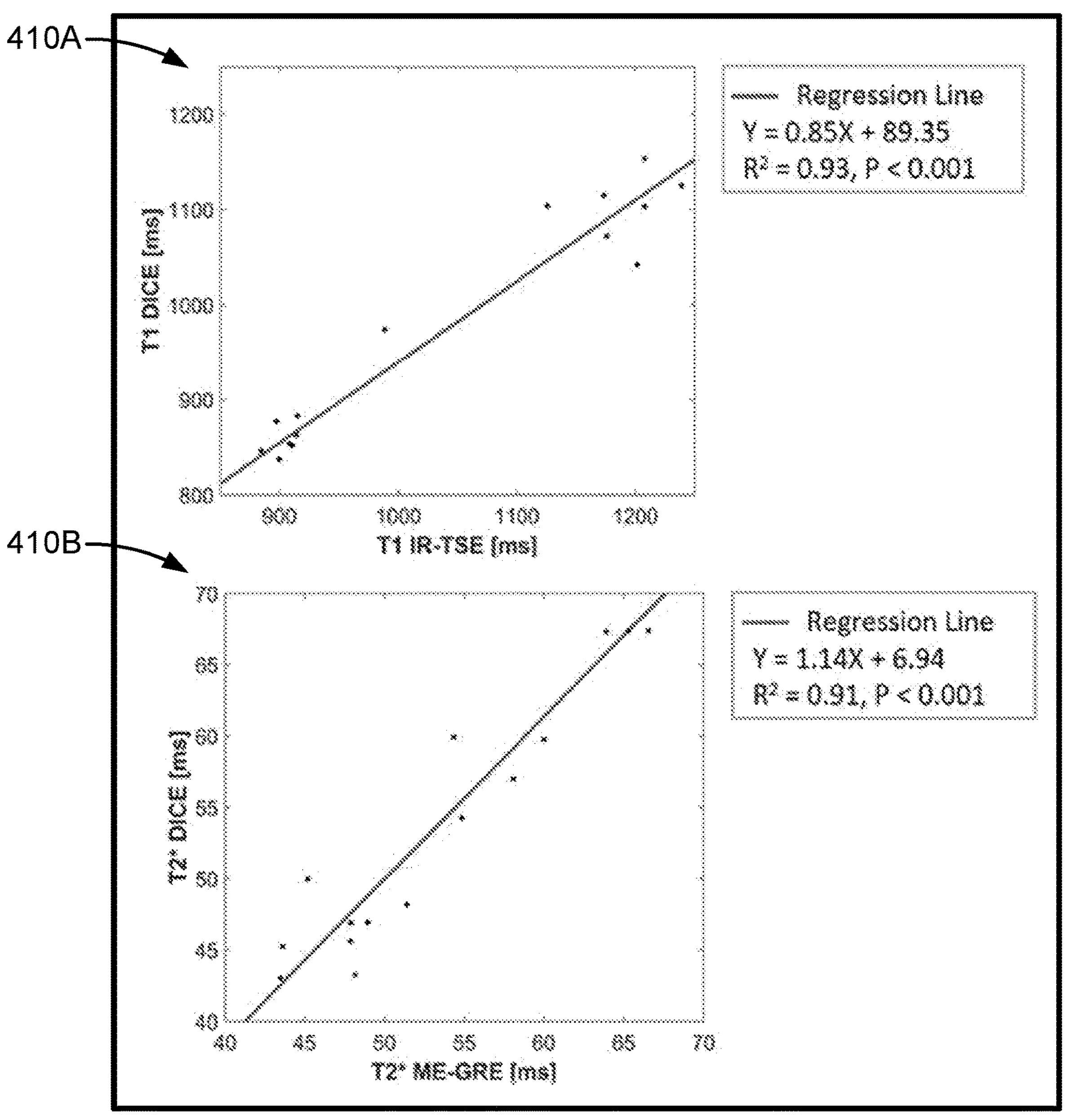
FIG. 4B shows T1 and T2* quantification comparing the method of FIG. 1 and conventional methods according to aspects of the present disclosure.

FIG. 4B shows a plot 410A of T1 quantifications for method 100 and a conventional reference method (such as IR-TSE); and a plot 410B of T2* quantification for method 100 and conventional reference method (such as MR-GRE). The plots 410A and 410B in FIG. 4B show that the results of method 100 that combines multiple imaging modalities are comparable to the results of conventional reference methods directed to only one modality.

Figures 5A, 5B:
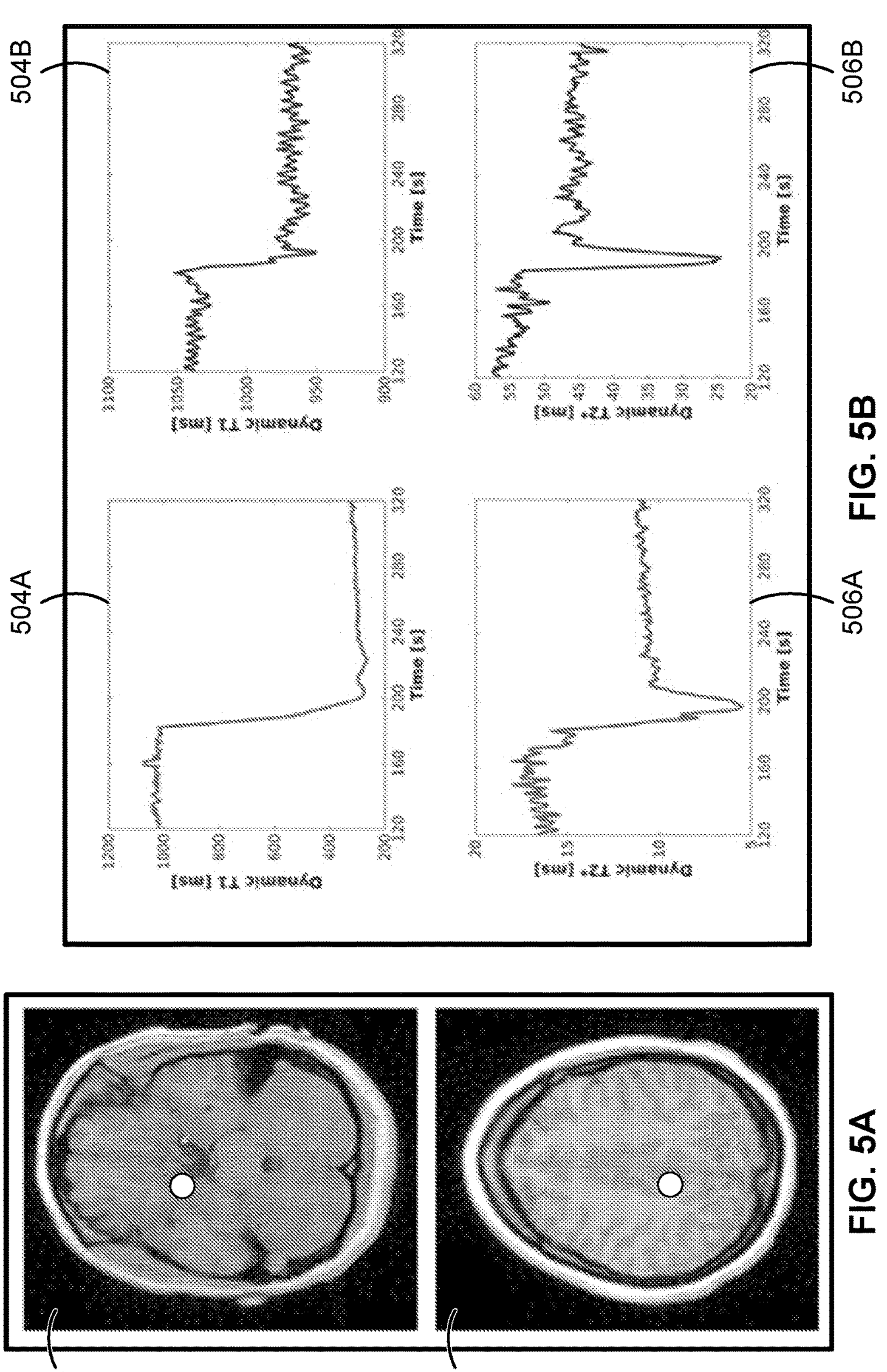
FIG. 5A shows post-contrast T1 W images constructed using the method of FIG. 1, according to aspects of the present disclosure.
FIG. 5B shows dynamic T1 and T2* curves acquired from the images of FIG. 5A, using the method of FIG. 1, according to aspects of the present disclosure.

FIG. 5A shows post-contrast T1-weighted images generated according to method 100. Image 502A shows blood, and image 502B shows normal tissue. The gray dots in images 502A and 502B identify the voxel of those images that is being analyzed. FIG. 5B shows dynamic T1 curves 504A and 504B. Dynamic T1 curve 504A represents the T1 parameter at the identified voxel of the blood image 502A, while dynamic T1 curve 504B represents the T1 parameter at the identified voxel of the tissue image 502B. FIG. 5B also shows dynamic T2* curves 506A and 506B. Dynamic T2* curve 506A represents the T2* parameter at the identified voxel of the blood image 502A, while dynamic T2* curve 506B represents the T2* parameter at the identified voxel of the tissue image 502B.

Figure 5C:
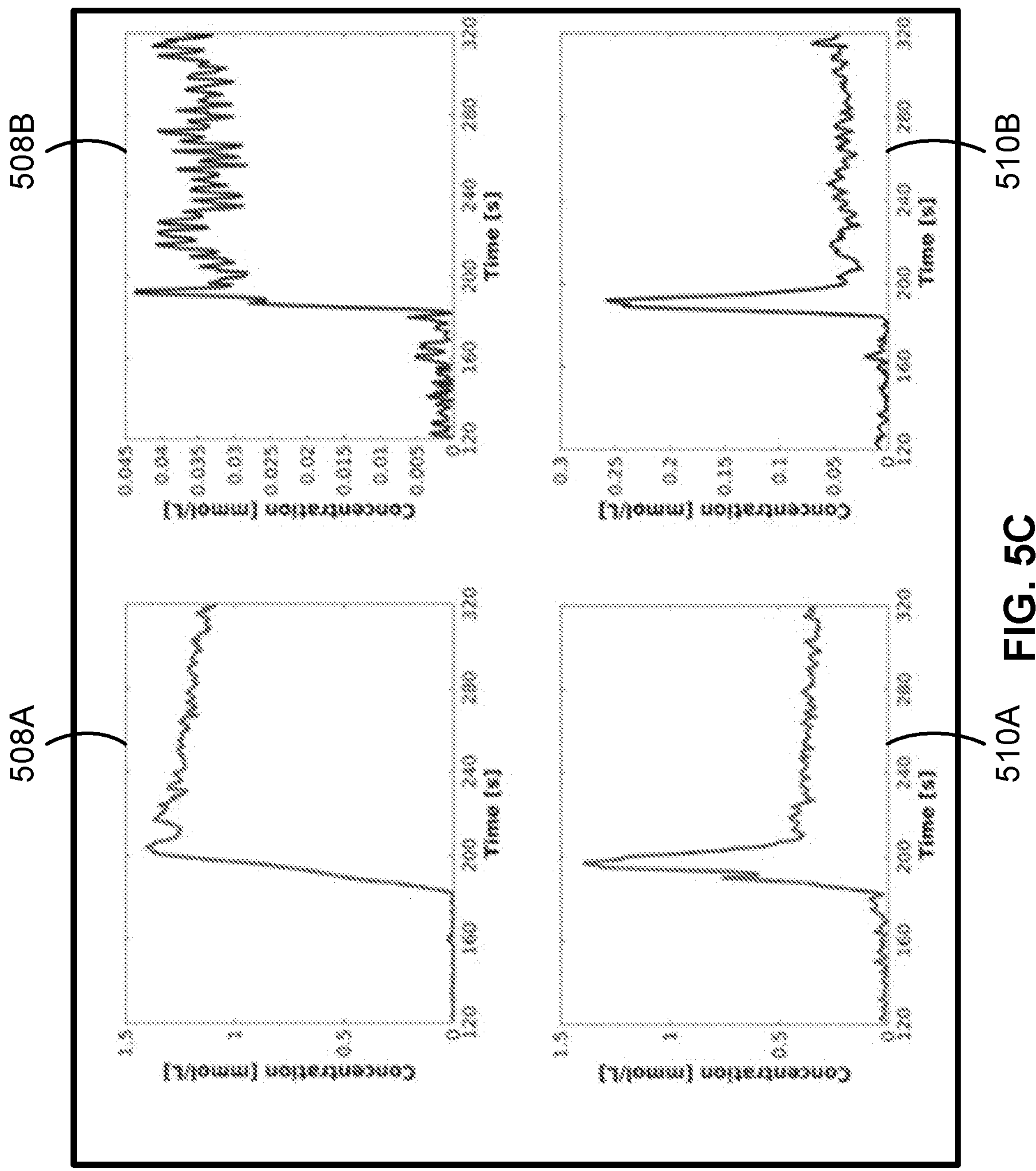
FIG. 5C shows T1-based and T2*-based contrast concentration curves obtained from the curves of FIG. 5B, according to aspects of the present disclosure.
Figure 5D:
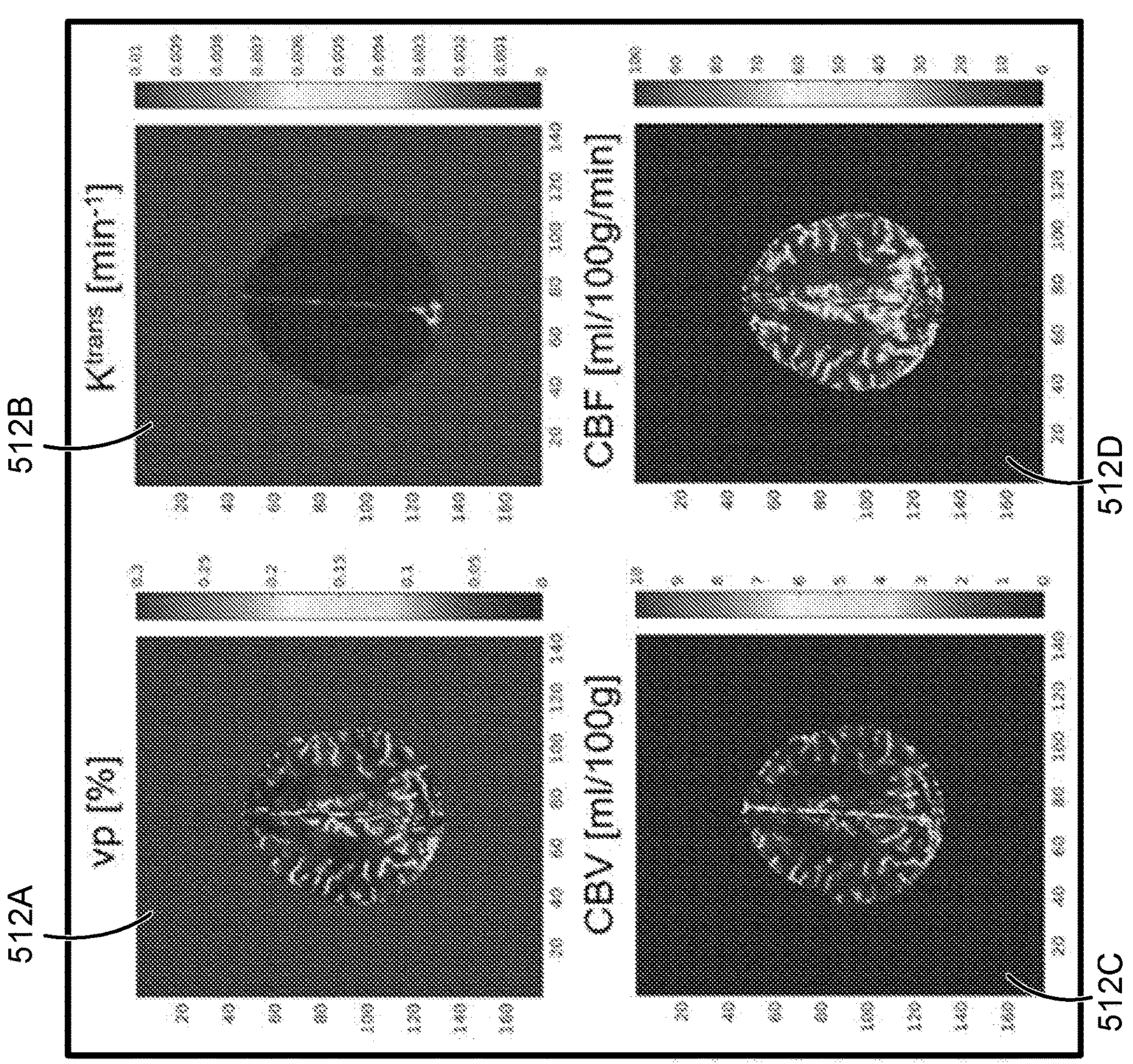
FIG. 5D shows permeability and perfusion maps generated using the method of FIG. 1, according to aspects of the present disclosure.

FIG. 5C shows T1-based (or R1-based) contrast concentration curves 508A and 508B, and T2*-based (or R2*-based) contrast concentration curves 510A and 510B. The T1-based concentration curves 508A and 508B were obtained based on the dynamic T1 curves 504A and 504B, respectively. The T2*-based concentration curves 510A and 510B were obtained based on the dynamic T2* curves 506A and 506B, respectively. Thus, concentration curves 508A and 510A represent the concentration of the contrast agent at the identified voxel of the blood image 502A, while concentration curves 508B and 510B represent the concentration of the contrast agent at the identified voxel of the tissue image 502B. FIG. 5D shows various different maps generated using method 100 on the same subject that the images and maps in FIGS. 5A, 5B, and 5C were generated from. Map 512A is a map of the fractional plasma volume. Map 512B is a map of the transfer constant. Map 512C is a map of the cerebral blood volume. Map 512D is a map of the cerebral blood flow.

Figure 6B:
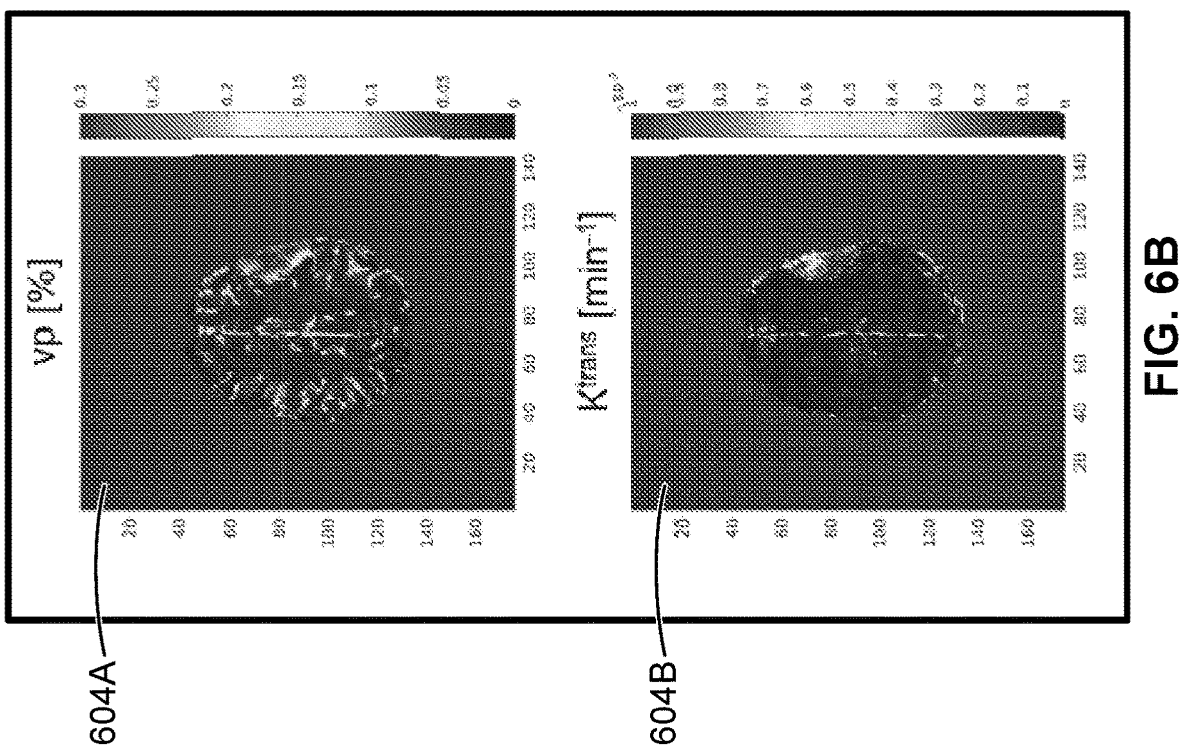
FIG. 6B shows fractional plasma volume and transfer constant maps of the subject with the meningioma obtained using the method of FIG. 1, according to aspects of the present disclosure.
Figure 6A:
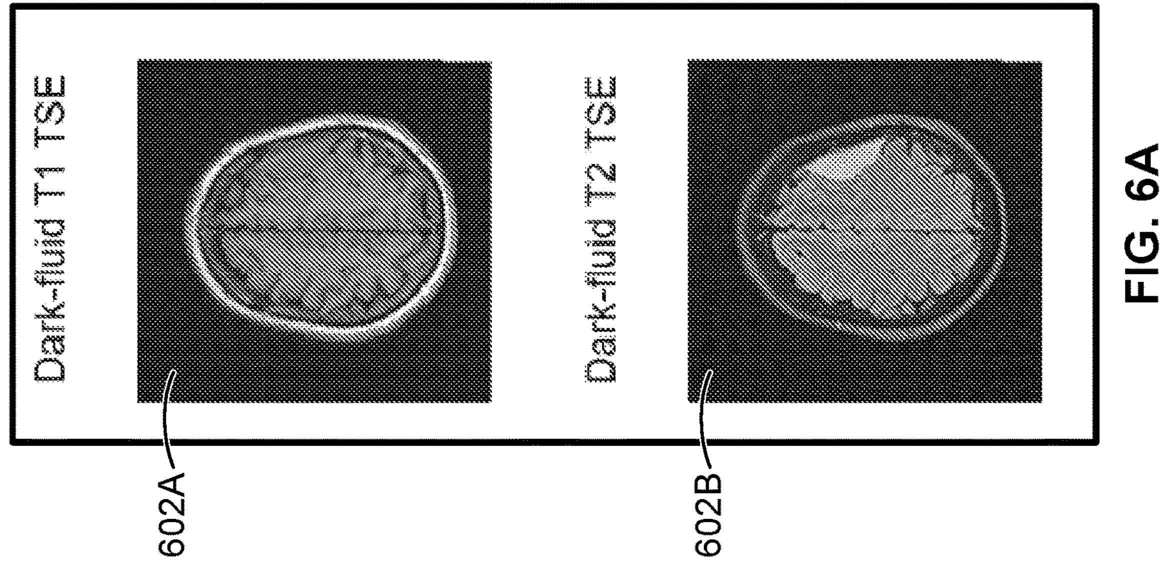
FIG. 6A shows dark-fluid T1 and T2* turbo spin echo images of a subject with a meningioma obtained using a conventional method.
Figure 6D:
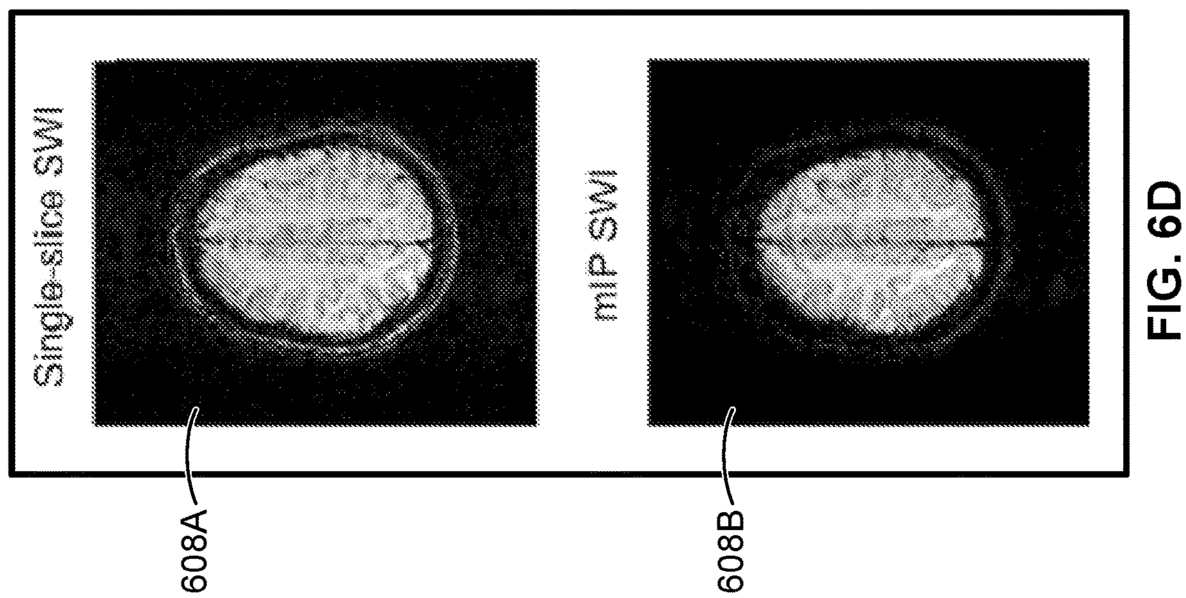
FIG. 6D shows susceptibility-weighted images of the subject with the meningioma obtained using the method of FIG. 1, according to aspects of the present disclosure.
Figure 6C:
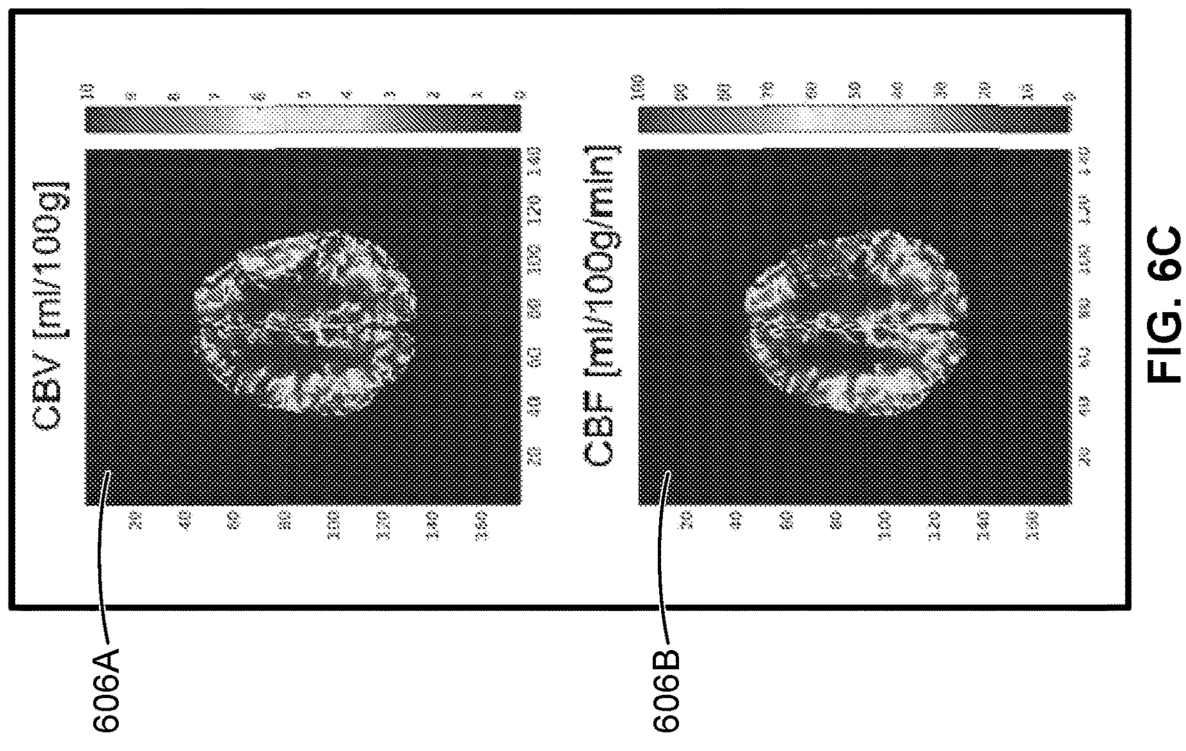
FIG. 6C shows cerebral blood volume and cerebral blood flow maps of the subject with the meningioma obtained using the method of FIG. 1, according to aspects of the present disclosure.

FIGS. 6A-6D show a variety of example images and parameter maps from a subject with a meningioma, which is a tumor that forms on the membranes that cover the brain on the inside of the skull. FIG. 6A shows a dark-fluid T1 turbo spin echo image 602A and a dark-fluid T2* turbo spin echo image 602B acquired using a conventional method. FIG. 6B shows a map 604A of the fractional plasma volume and a map 604B of the transfer constant of the same subject generated using method 100. FIG. 6C shows a map 606A of the cerebral blood volume and a map 606B of the cerebral blood flow of the same subject generated using method 100. FIG. 6D shows a single-slice SW image 608A and a minimum intensity projection (mIP) SW image 608B of the same subject generated using method 100. Because meningiomas are highly vascularized and perfused, and have no endothelial tight junctions that could serve as permeability barriers, maps 604A, 604B, 606A, 606B confirm an increase in the fractional plasma volume, the transfer constant, the cerebral blood volume, and the cerebral blood flow, respectively, in the area where the meningioma is located. The SW images 608A, 608B indicate a lack of no intra-tumor bleeding within the meningioma.

Figure 7B:
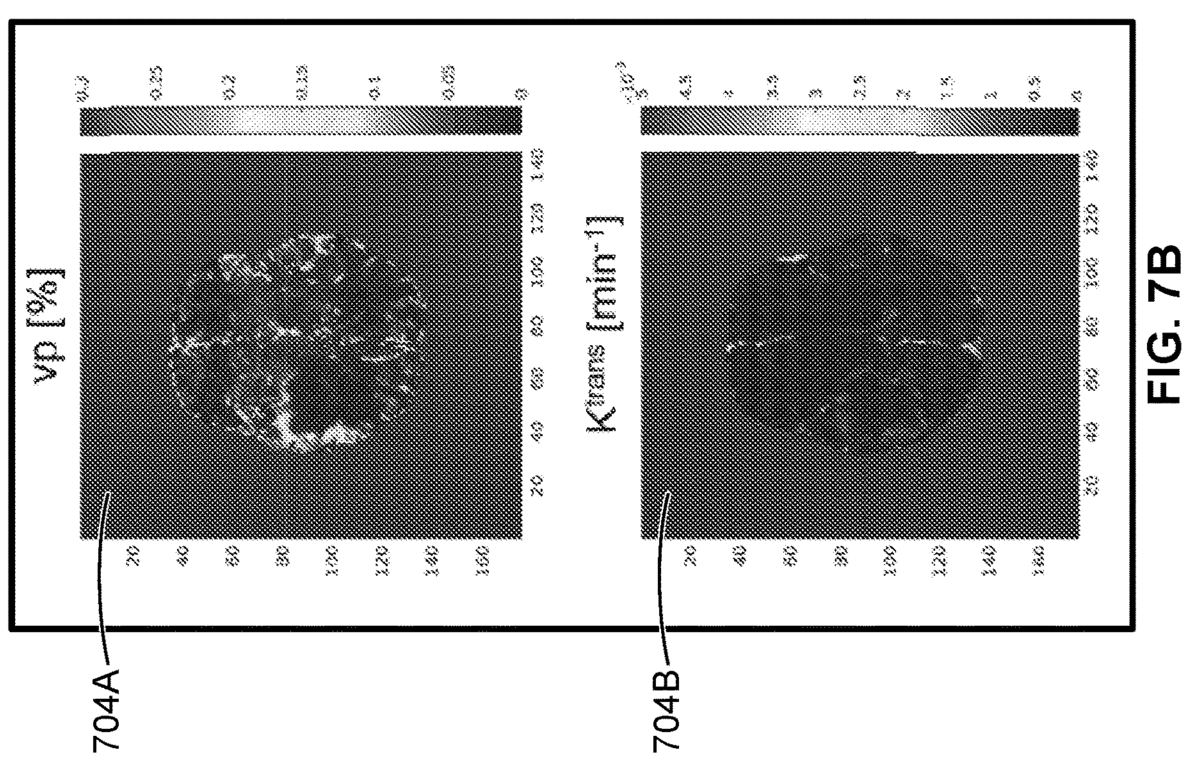
FIG. 7B shows fractional plasma volume and transfer constant maps of the subject with the intracranial hematoma obtained using the method of FIG. 1, according to aspects of the present disclosure.
Figure 7A:
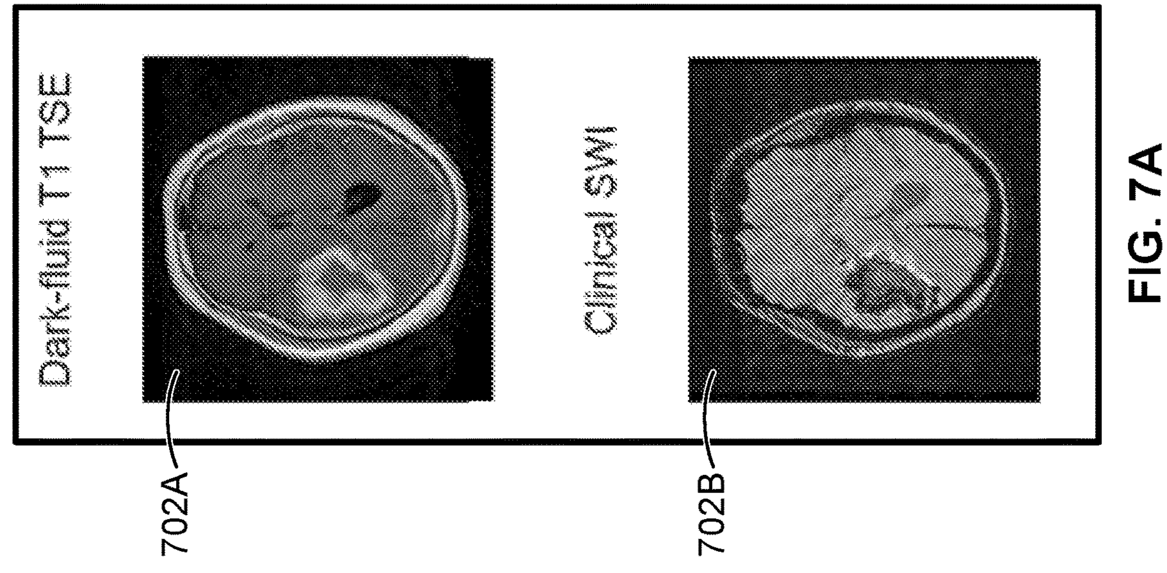
FIG. 7A shows dark-fluid T1 turbo spin echo and susceptibility-weighted images of a subject with an intracranial hematoma obtained using a conventional method.
Figure 7D:
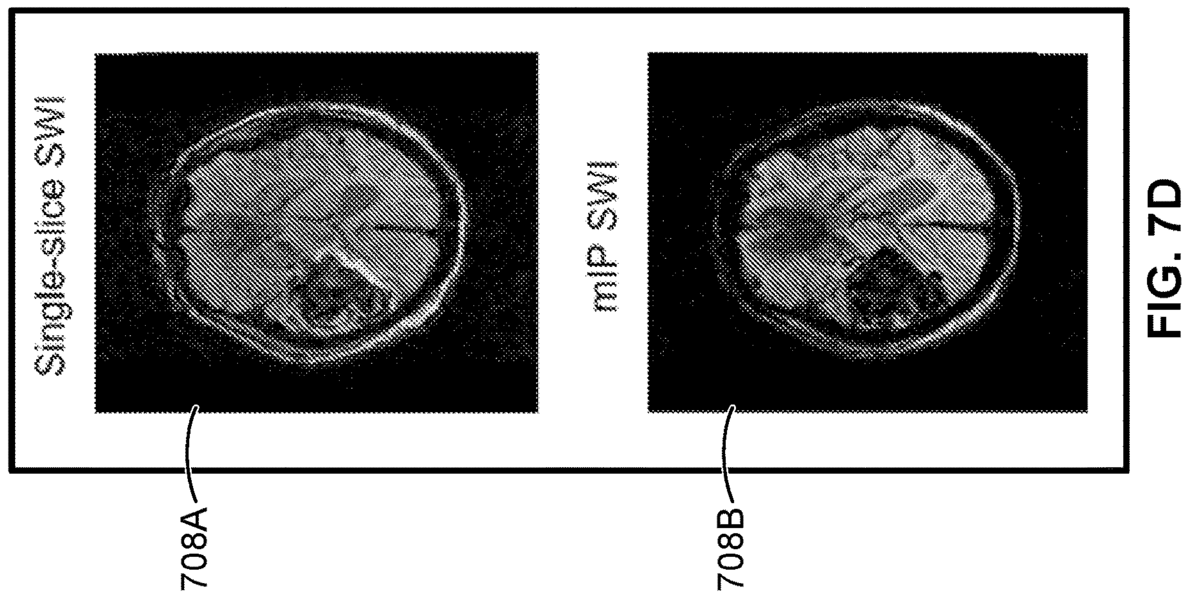
FIG. 7D shows susceptibility-weighted images of the subject with the intracranial hematoma obtained using the method of FIG. 1, according to aspects of the present disclosure.
Figure 7C:
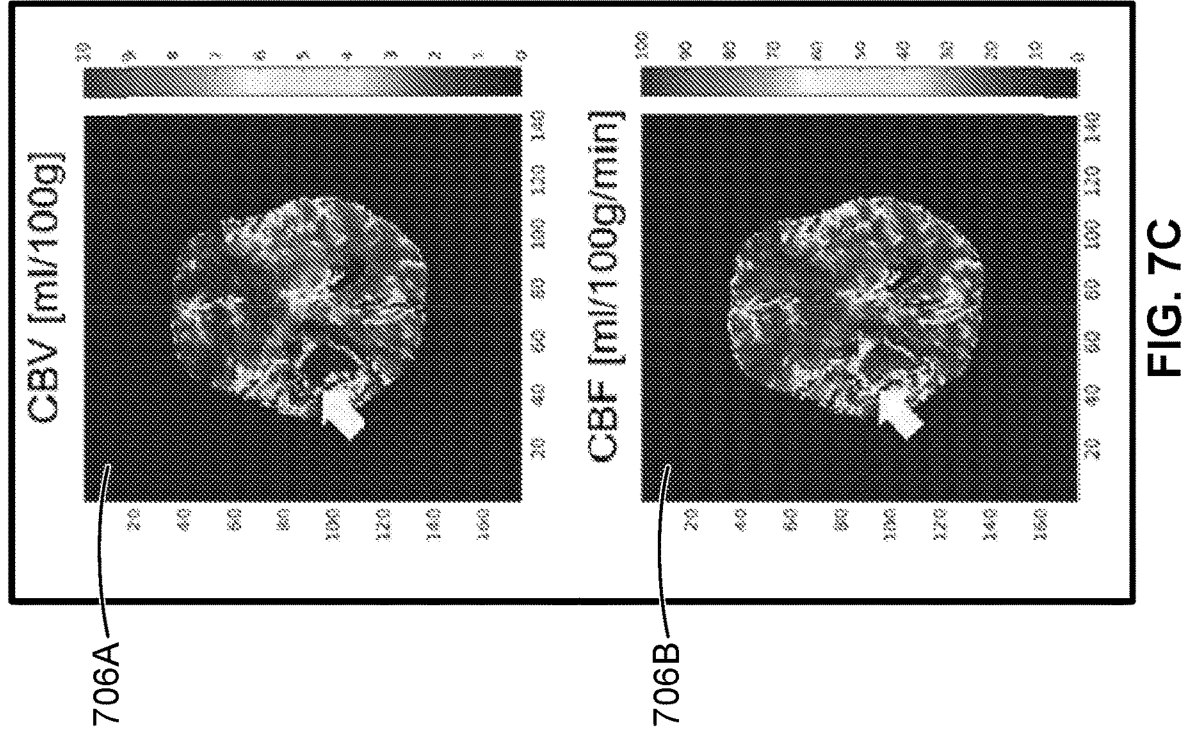
FIG. 7C shows cerebral blood volume and cerebral blood flow maps of the subject with the intracranial hematoma obtained using the method of FIG. 1, according to aspects of the present disclosure.

FIGS. 7A-7D show a variety of example images and parameter maps from a subject with an intracranial hematoma. FIG. 7A shows a dark-fluid T1 turbo spin echo image 702A and a SW image 702B acquired using a conventional method. FIG. 7B shows a map 704A of the fractional plasma volume and a map 704B of the transfer constant of the same subject generated using method 100. FIG. 7C shows a map 706A of the cerebral blood volume and a map 706B of the cerebral blood flow of the same subject generated using method 100. FIG. 7D shows a single-slice SW image 708A and an mIP SW image 708B of the same subject generated using method 100. The maps 704A, 704B of the fractional plasma volume and the transfer constant show lower values inside the hematoma than in the adjacent tissue, which suggests hemostasis in this area. The maps 706A, 706B of the cerebral blood volume and cerebral blood flow show lower values within the hematoma, which shows potential damage to normal tissue due to compression of the blood. The SW images 708A, 708B obtained using method 100 clearly depict the hematoma, which is consistent with images 702A, 702B obtained using the conventional method.

Figure 8:
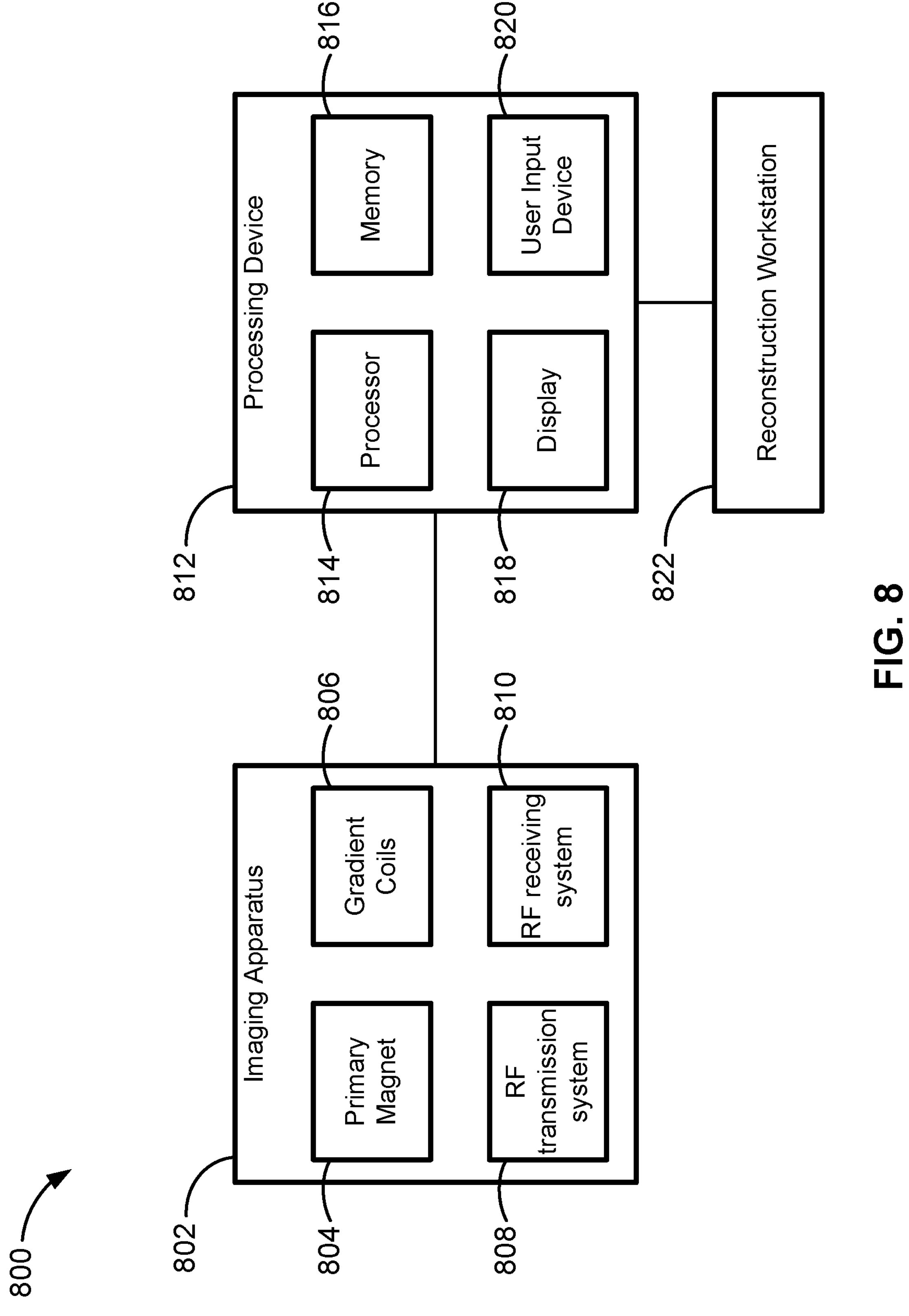
FIG. 8 shows a system for performing magnetic resonance imaging, according to aspects of the present disclosure.

Aspects of the present disclosure can be implemented using a variety of hardware. One such implementation is illustrated in FIG. 8. A system 800 for performing magnetic resonance imaging on a subject includes an imaging apparatus 802, a processing device 812, and a reconstruction workstation 822. The imaging apparatus 802 can be one used for standard magnetic resonance imaging, and can include a primary magnet 804, gradient coils 806, an RF transmission system 808, and an RF receiving system 810. The primary magnet 804 can be a permanent magnet, an electromagnet (such as a coil), or any other suitable magnet. Primary magnet 804 is used to create the external magnet field that is applied to the sample during imaging. Gradient coils 806 create a secondary magnet field that distorts the external magnetic field and can cause the resonant frequency of the protons in the sample to vary by position. The gradient coils 806 can thus be used to spatially encode the positions of protons throughout the sample, e.g. can be used to select which plane intersecting the sample will be used for imaging.

The RF transmission system 808 is used to apply the RF pulse sequence that provides energy to the protons in the sample to rotate their magnet moments out of alignment with the external magnetic field, and saturates the solute material protons. The RF transmission system 808 generally includes a frequency generator (such as an RF synthesizer), a power amplifier, and a transmitting coil. The RF receiving system 810 receives the signals emitted by the protons in the sample as they relax back to their standard alignment. The RF receiving system 810 can a receiving coil to receive the emitted signals, and a pre-amplifier for boosting the received signals and ensuring the signals are suitable for processing. In some implementations, the RF receiving system 810 can include a signal processing component that processes the received signals to provide data that is usable by the processing device 812. Each of the component of the imaging apparatus can be disposed within one or more housings. In some implementations, the imaging apparatus 802 is a 3.0 Tesla clinical scanner equipped with an 18-channel phase array body coil.

The processing device 812 can be communicatively coupled to the imaging apparatus 802, and can include a processor 814, processor-executable memory 816, a display 818, and a user input device 820. The processing device 812 is used to manage the operations of the imaging apparatus 802, and can thus be configured to cause the imaging apparatus 802 to perform dynamic imaging according to the principles disclosed herein. The memory 816 can contain instructions that when executed by processor 814, cause the imaging apparatus 802 to operate as desired. The memory 816 can also store the data obtained from the MRI sequence.

The reconstruction workstation 822 is generally a separate processing device or system that receives the imaging data from the processing device 812. The reconstruction workstation can be configured as necessary to perform any analysis of the data, include any or all of the steps in method 100. In some implementations, the neural network is implemented on the reconstruction workstation 822. In other implementations, the neural network is implemented on separate hardware that can communicate with the reconstruction workstation 822.

In some implementations, a non-transitory, machine-readable medium has instructions stored thereon for implementing any of any of the methods or processes discussed herein. A machine processor is configured to executed the instructions in order to perform these methods or processes.

Aspects of the present disclosure can be implemented on a variety of types of processing devices, such as general purpose computer systems, microprocessors, digital signal processors, micro-controllers, application specific integrated circuits (ASICs), programmable logic devices (PLDs) field programmable logic devices (FPLDs), programmable gate arrays (PGAs), field programmable gate arrays (FPGAs), mobile devices such as mobile telephones, personal digital assistants (PDAs), or tablet computers, local servers, remote servers, wearable computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read only memory (ROM) in the system or a floppy disk, hard disk, CD ROM, DVD ROM, flash, or other computer readable medium that is read from and/or written to by a magnetic, optical, or other reading and/or writing system that is coupled to the processing device, can be used for the memory or memories.

While aspects of the present disclosure have been described with reference to one or more particular implementations, those skilled in the art will recognize that many changes may be made thereto without departing from the spirit and scope of the present disclosure. Each of these implementations and obvious variations thereof are contemplated as falling within the spirit and scope of the present disclosure. It is also contemplated that additional implementations according to aspects of the present disclosure may combine any number of features from any of the implementations described herein.

What is claimed is:

1. A method for performing magnetic resonance (MR) imaging on a subject, the method comprising:

injecting a contrast agent into a region of interest of the subject;

applying a pulse sequence to the region of interest of the subject, wherein the pulse sequence comprises a plurality of repetition time periods, each repetition time period including: (i) a non-selective saturation recovery preparation pulse to generate T1 recovery along a magnetization z-axis, (ii) a plurality of excitation pulses, and (iii) a plurality of sets of readout lines, each set of readout lines following one of the excitation pulses and including two or more readout lines, the readout lines of each set following a T2* decay, thereby forming multi-echo fast low-angle shot (FLASH) readouts;

collecting auxiliary data for the region of interest of the subject, the auxiliary data being related to one or more time-varying parameters of the subject within the region of interest;

determining a temporal factor $\Phi$ from the auxiliary data;

collecting imaging data for the region of interest of a brain of the subject, the imaging data being related to one or more spatially-varying parameters of the brain within the region of interest;

determining a spatial factor $U_r$ from the imaging data;

modeling a multi-dimensional image sequence as $I=U_r\Phi$, denoted as I(r, rT1, tT2*, tCE), where tT1 refers to T1 recovery, tT2* refers to T2* decay, and tCE refers to a contrast enhancement time course;

deriving dynamic T1 and T2* maps from the multi-dimensional image sequence; and deriving at least a first metric and a second metric from the dynamic T1 and T2* maps, the first metric being a kinetic parameter associated with dynamic contrast enhanced (DCE) imaging comprising (i) a fractional plasma volume $v_p$ of the region of interest, (ii) a fractional extravascular-extracellular volume $v_e$ of the region of interest, (iii) a transfer constant $K^{trans}$ of the region of interest, or (iv) any combination of (i)-(iii), and the second metric being a hemodynamic parameter associated with dynamic susceptibility contrast (DSC) imaging comprising (i) a cerebral blood volume (CBV) measurement, (ii) a cerebral blood flow measurement, or (iii) any combination of (i)-(ii).

2. The method of claim 1, wherein the spatial factor $U_r$ is determined by fitting the temporal factor $\Phi$ to the collected imaging data.

3. The method of claim 1, wherein the temporal factor $\Phi$ is fitted to the collected imaging data according to:

$$\hat{U}_r = \text{argmin}_{U_r}\|d - \Omega[EU_r\Phi]\|_2^2 + \lambda R(U_r),$$

wherein $\Omega$ is an undersampling pattern, E is a signal model, R(•) is a regularization function, and $\lambda$ is a regularization parameter of the regularization function R(•).

4. The method of claim 1, wherein the fractional plasma volume $v_p$ of the region of interest, the fractional extravascular-extracellular volume $v_e$ of the region of interest, and the transfer constant $K^{trans}$ of the region of interest are derived according to:

wherein $$C_t^{R1}(t)$$

is a T1-based concentration of the contrast agent in tissue in the region of interest and $$C_p^{R1}(t)$$

is the T1-based concentration of the contrast agent in plasma in the region of interest.

5. The method of claim 1, wherein the T1-based concentration of the contrast agent in tissue and the T1-based concentration of the contrast agent in plasma are derived from dynamic T1 and T2* maps generated from the multi-dimensional image sequence I.

6. The method of claim 1, wherein the cerebral blood volume measurement is a leakage-corrected cerebral blood volume measurement.

7. The method of claim 6, wherein the cerebral blood volume measurement is derived according to:

$$CBV = \frac{100}{\rho}\cdot\frac{(1-H_{SV})}{(1-H_{LV})}\cdot\frac{\int C_t^{R2^*(t)}(t)dt}{\int C_a^{R2^*(t)}(t)dt},$$

wherein $$C_a^{R2^*(t)}$$

is a T2*-based concentration of the contrast agent in a feeding artery in the region of interest, $$C_t^{R2^*(t)}$$

is a T2*-based concentration of the contrast agent in tissue of the region of interest, $\rho$ is a density of a brain of the subject, $H_{SV}$ is a correction to a volume hematocrit level in small blood vessels of the subject, and $H_{LV}$ is a correction to a volume hematocrit level in large blood vessels of the subject.

8. The method of claim 1, wherein the cerebral blood flow measurement is a leakage-corrected cerebral blood flow measurement.

9. The method of claim 8, wherein the cerebral blood flow measurement is derived according to:

$$CBF = 60\cdot\frac{100}{\rho}\cdot\frac{(1-H_{SV})}{(1-H_{LV})}\cdot\left[\max\left(C_t^{R2^*}(t)\otimes^{-1}C_a^{R2^*}(t)\right)\right],$$

wherein $$c_a^{R2^*(t)}$$

is a T2*-based concentration of the contrast agent in a feeding artery of the region of interest, $$C_t^{R2^*(t)}$$

is a T2*-based concentration of the contrast agent in tissue of the region of interest, $\otimes^{-1}$ is a deconvolution operation, p is a density of a brain of the subject, $H_{SV}$ is a correction to a volume hematocrit level in small blood vessels of the subject, and $H_{LV}$ is a correction to a volume hematocrit level in large blood vessels of the subject.

10. The method of claim 1, wherein the first metric is associated with susceptibility weighted (SW) imaging.

11. The method of claim 10, wherein the first metric is one or more SW images.

12. The method of claim 11, wherein the method further comprises:

generating an image from a final readout line of each set of readout lines; and multiplying a magnitude of the generated images by a corresponding phase mask to generate the one or more SW images.

13. The method of claim 1, further comprising fitting the multi-dimensional image sequence to a signal equation to generate T1 and T2* maps.

14. The method of claim 13, wherein the signal equation is given by:

$$S(A, \alpha, B, n, TE, T1(t), T2^*(t)) = A\frac{1-e^{-\frac{TR}{T1(t)}}}{1-e^{1\frac{TR}{T1(t)}}\cos(\alpha)}\left[1+(B-1)(e^{-\frac{TR}{T1(t)}}\cos(\alpha)^n\right]e^{-\frac{TE}{T2^*(t)}}\sin(\alpha).$$

15. The method of claim 13, further comprising generating a dynamic T1 curve based at least in part on the T1 map, and a dynamic T2* curve based at least in part on the T2* map.

16. The method of claim 15, further comprising generating an R1-based concentration of the contrast agent based at least in part on the dynamic T1 curve.

17. The method of claim 16, further comprising generating, based at least in part on the T1-based concentration of the contrast agent, (i) a fractional plasma volume $v_p$ of the region of interest, (ii) a fractional extravascular-extracellular volume $v_e$ of the region of interest, (iii) a transfer constant $K^{trans}$ of the region of interest, or (iv) any combination of (i)-(iii).

18. The method of claim 16, further comprising generating an R2*-based concentration of the contrast agent based at least in part on the dynamic T2* curve.

19. The method of claim 18, further comprising generating, based at least in part on the R2*-based concentration of the contrast agent, (i) a leakage-corrected cerebral blood volume measurement, (ii) a leakage-corrected cerebral blood flow measurement, or (iii) both (i) and (ii).

20. A system for performing magnetic resonance (MR) imaging on a subject, comprising:

a magnet operable to provide a magnetic field;

a transmitter operable to transmit to a region within the magnetic field;

a receiver operable to receive a magnetic resonance signal from the region with the magnetic field; and one or more processors operable to control the transmitter and the receiver, the one or more processors being configured to cause the following method to be performed:

injecting a contrast agent into a region of interest of the subject;

applying a pulse sequence to the region of interest of the subject, wherein the pulse sequence comprises a plurality of repetition time periods, each repetition time period including: (i) a non-selective saturation recovery preparation pulse to generate T1 recovery along a magnetization z-axis, (ii) a plurality of excitation pulses, and (iii) a plurality of sets of readout lines, each set of readout lines following one of the excitation pulses and including two or more readout lines, the readout lines of each set following a T2* decay, thereby forming multi-echo fast low-angle shot (FLASH) readouts;

collecting auxiliary data for the region of interest of the subject, the auxiliary data being related to one or more time-varying parameters of the subject within the region of interest;

determining a temporal factor Φ from the auxiliary data;

collecting imaging data for the region of interest of a brain of the subject, the imaging data being related to one or more spatially-varying parameters of the brain within the region of interest;

determining a spatial factor $U_r$ from the imaging data;

modeling a multi-dimensional image sequence as $I=U_r\Phi$, denoted as I(r, rT1, tT2*, tCE), where tT1 refers to T1 recovery, tT2* refers to T2* decay, and tCE refers to a contrast enhancement time course;

deriving dynamic T1 and T2* maps from the multi-dimensional image sequence; and deriving at least a first metric and a second metric from the dynamic T1 and T2* maps, the first metric being a kinetic parameter associated with dynamic contrast enhanced (DCE) imaging comprising (i) a fractional plasma volume $v_p$ of the region of interest, (ii) a fractional extravascular-extracellular volume $v_e$ of the region of interest, (iii) a transfer constant $K^{trans}$ of the region of interest, or (iv) any combination of (i)-(iii), and the second metric being a hemodynamic parameter associated with dynamic susceptibility contrast (DSC) imaging comprising (i) a cerebral blood volume (CBV) measurement, (ii) a cerebral blood flow measurement, or (iii) any combination of (i)-(ii).

21. A non-transitory machine-readable medium having stored thereon instructions for performing magnetic resonance (MR) imaging on a subject, which when executed by at least one processor, cause the following method to be performed:

injecting a contrast agent into a region of interest of the subject;

applying a pulse sequence to the region of interest of the subject, wherein the pulse sequence comprises a plurality of repetition time periods, each repetition time period including: (i) a non-selective saturation recovery preparation pulse to generate T1 recovery along a magnetization z-axis, (ii) a plurality of excitation pulses, and (iii) a plurality of sets of readout lines, each set of readout lines following one of the excitation pulses and including two or more readout lines, the readout lines of each set following a T2* decay, thereby forming multi-echo fast low-angle shot (FLASH) readouts;

collecting auxiliary data for the region of interest of a brain of the subject, the auxiliary data being related to one or more time-varying parameters of the brain within the region of interest;

determining a temporal factor Φ from the auxiliary data;

collecting imaging data for the region of interest of the subject, the imaging data being related to one or more spatially-varying parameters of the subject within the region of interest;

determining a spatial factor $U_r$ from the imaging data;

modeling a multi-dimensional image sequence as $I=U_r\Phi$, denoted as I(r, rT1, tT2*, tCE), where tT1 refers to T1 recovery, tT2* refers to T2* decay, and tCE refers to a contrast enhancement time course;

deriving dynamic T1 and T2* maps from the multi-dimensional image sequence; and deriving at least a first metric and a second metric from the dynamic T1 and T2* maps, the first metric being a kinetic parameter associated with dynamic contrast enhanced (DCE) imaging comprising (i) a fractional plasma volume $v_p$ of the region of interest, (ii) a fractional extravascular-extracellular volume $v_e$ of the region of interest, (iii) a transfer constant $K^{trans}$ of the region of interest, or (iv) any combination of (i)-(iii), and the second metric being a hemodynamic parameter associated with dynamic susceptibility contrast (DSC) imaging comprising (i) a cerebral blood volume (CBV) measurement, (ii) a cerebral blood flow measurement, or (iii) any combination of (i)-(ii).

* * * * *